US008652201B2

(12) United States Patent
Oberti et al.

(10) Patent No.: US 8,652,201 B2
(45) Date of Patent: Feb. 18, 2014

(54) APPARATUS AND METHOD FOR TREATING CARDIOVASCULAR DISEASES

(75) Inventors: Carlos Oberti, Chagrin Falls, OH (US); Jose L. Navia, Shaker Heights, OH (US); Richard Krasuski, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 63 days.

(21) Appl. No.: 12/357,520

(22) Filed: Jan. 22, 2009

(65) Prior Publication Data

US 2009/0177262 A1    Jul. 9, 2009

Related U.S. Application Data

(63) Continuation-in-part of application No. 11/789,827, filed on Apr. 26, 2007.

(60) Provisional application No. 60/795,256, filed on Apr. 26, 2006.

(51) Int. Cl.
*A61F 2/06* (2013.01)

(52) U.S. Cl.
USPC ......... 623/1.42; 623/1.3; 623/1.31; 623/1.46; 623/2.17; 623/2.18

(58) Field of Classification Search
USPC .................... 623/1.12, 1.15, 1.18, 1.25, 1.36, 623/1.42–1.43, 1.46, 2.36, 1.44, 1.3, 1.31, 623/2.17, 2.18
See application file for complete search history.

(56) References Cited

U.S. PATENT DOCUMENTS

| | | | |
|---|---|---|---|
| 3,898,701 A * | 8/1975 | La Russa | 623/2.17 |
| 5,178,618 A | 1/1993 | Kandarpa | |
| 5,911,733 A * | 6/1999 | Parodi | 623/1.15 |
| 6,012,457 A * | 1/2000 | Lesh | 128/898 |
| 6,120,534 A * | 9/2000 | Ruiz | 623/1.19 |
| 6,132,384 A | 10/2000 | Christopherson et al. | |
| 6,415,183 B1 | 7/2002 | Scheiner et al. | |
| 6,416,548 B2 | 7/2002 | Chinn et al. | |
| 6,522,926 B1 | 2/2003 | Kieval et al. | |
| 6,610,713 B2 | 8/2003 | Tracey | |
| 6,632,223 B1 * | 10/2003 | Keane | 606/41 |
| 6,633,779 B1 | 10/2003 | Schuler et al. | |
| 6,685,739 B2 * | 2/2004 | DiMatteo et al. | 623/1.24 |
| 6,716,242 B1 | 4/2004 | Altman | |
| 6,805,706 B2 * | 10/2004 | Solovay et al. | 623/1.15 |
| 6,926,714 B1 | 8/2005 | Sra | |

(Continued)

*Primary Examiner* — Thomas J Sweet
*Assistant Examiner* — Seema Mathew
(74) *Attorney, Agent, or Firm* — Tarolli, Sundheim, Covell & Tummino LLP

(57) ABSTRACT

A method is provided for treating a cardiovascular disease, such as pulmonary arterial hypertension, an arrhythmia, or heart failure. One step of the method includes providing an apparatus. The apparatus includes an expandable support member having oppositely disposed proximal and distal end portions and a main body portion extending between the end portions. The proximal end portion includes a plurality of wing members extending from the main body portion. At least a portion of the expandable support member is treated with at least one therapeutic agent for eluting into a blood vessel. The expandable support member is inserted into the pulmonary vasculature and then advanced to a bifurcation in the pulmonary vasculature. The bifurcation includes the intersection of a first pulmonary vessel, a second pulmonary vessel, and a third pulmonary vessel. The expandable support member is secured at the bifurcation to treat pulmonary arterial hypertension, for example.

25 Claims, 24 Drawing Sheets

(56) References Cited

U.S. PATENT DOCUMENTS

| | | | |
|---|---|---|---|
| 6,953,476 B1* | 10/2005 | Shalev | 623/1.15 |
| 7,149,574 B2 | 12/2006 | Yun et al. | |
| 7,194,313 B2 | 3/2007 | Libbus | |
| 7,195,628 B2* | 3/2007 | Falkenberg | 606/41 |
| 7,245,971 B2 | 7/2007 | Park et al. | |
| 7,273,055 B2 | 9/2007 | Danek et al. | |
| 7,363,076 B2 | 4/2008 | Yun et al. | |
| 7,418,292 B2 | 8/2008 | Shafer | |
| 7,914,569 B2* | 3/2011 | Nguyen et al. | 623/1.18 |
| 8,252,042 B2* | 8/2012 | McNamara et al. | 623/1.26 |
| 8,252,051 B2* | 8/2012 | Chau et al. | 623/2.12 |
| 8,257,376 B2* | 9/2012 | Solem | 606/167 |
| 8,409,268 B2* | 4/2013 | Swanson et al. | 623/1.11 |
| 2002/0082682 A1 | 6/2002 | Barclay et al. | |
| 2003/0055491 A1 | 3/2003 | Schwartz et al. | |
| 2003/0069606 A1 | 4/2003 | Girouard et al. | |
| 2003/0074055 A1* | 4/2003 | Haverkost | 623/1.16 |
| 2003/0139805 A1* | 7/2003 | Holmberg et al. | 623/1.31 |
| 2004/0082989 A1* | 4/2004 | Cook et al. | 623/1.13 |
| 2004/0098106 A1 | 5/2004 | Williams et al. | |
| 2004/0116965 A1* | 6/2004 | Falkenberg | 607/5 |
| 2004/0122506 A1 | 6/2004 | Shanley et al. | |
| 2004/0153139 A1 | 8/2004 | Altman | |
| 2004/0158313 A1* | 8/2004 | Altman | 623/1.15 |
| 2004/0167598 A1* | 8/2004 | Margolis | 623/1.11 |
| 2004/0215186 A1 | 10/2004 | Cornelius et al. | |
| 2004/0220655 A1* | 11/2004 | Swanson et al. | 623/1.11 |
| 2004/0243230 A1 | 12/2004 | Navia et al. | |
| 2004/0249443 A1 | 12/2004 | Shanley et al. | |
| 2004/0254597 A1 | 12/2004 | Schwartz et al. | |
| 2005/0070952 A1* | 3/2005 | Devellian | 606/200 |
| 2005/0090820 A1 | 4/2005 | Cornelius et al. | |
| 2005/0177118 A1 | 8/2005 | Hoganson et al. | |
| 2005/0228496 A1 | 10/2005 | Mensah et al. | |
| 2005/0234540 A1* | 10/2005 | Peavey et al. | 623/1.18 |
| 2005/0267567 A1* | 12/2005 | Shalev | 623/1.31 |
| 2006/0009838 A1 | 1/2006 | Shanley et al. | |
| 2006/0047338 A1* | 3/2006 | Jenson et al. | 623/2.11 |
| 2007/0129637 A1* | 6/2007 | Wolinsky et al. | 600/486 |
| 2007/0191902 A1 | 8/2007 | Errico et al. | |
| 2010/0010623 A1* | 1/2010 | Lashinski et al. | 623/1.24 |
| 2011/0208297 A1* | 8/2011 | Tuval et al. | 623/2.17 |
| 2011/0208298 A1* | 8/2011 | Tuval et al. | 623/2.17 |
| 2011/0264196 A1* | 10/2011 | Savage et al. | 623/1.26 |
| 2011/0319988 A1* | 12/2011 | Schankereli et al. | 623/2.11 |
| 2012/0053685 A1* | 3/2012 | Cerf et al. | 623/2.17 |
| 2012/0078347 A1* | 3/2012 | Braido et al. | 623/1.26 |
| 2012/0089224 A1* | 4/2012 | Haug et al. | 623/2.17 |
| 2012/0158129 A1* | 6/2012 | Duffy et al. | 623/2.11 |
| 2012/0179244 A1* | 7/2012 | Schankereli et al. | 623/2.11 |
| 2012/0265296 A1* | 10/2012 | McNamara et al. | 623/2.17 |
| 2012/0316642 A1* | 12/2012 | Yu et al. | 623/2.13 |
| 2012/0323316 A1* | 12/2012 | Chau et al. | 623/2.18 |
| 2013/0190861 A1* | 7/2013 | Chau et al. | 623/2.18 |
| 2013/0211508 A1* | 8/2013 | Lane et al. | 623/2.11 |

* cited by examiner

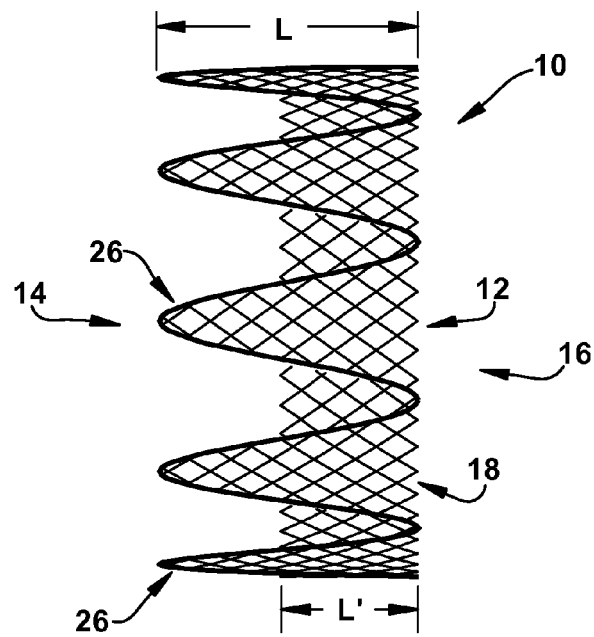
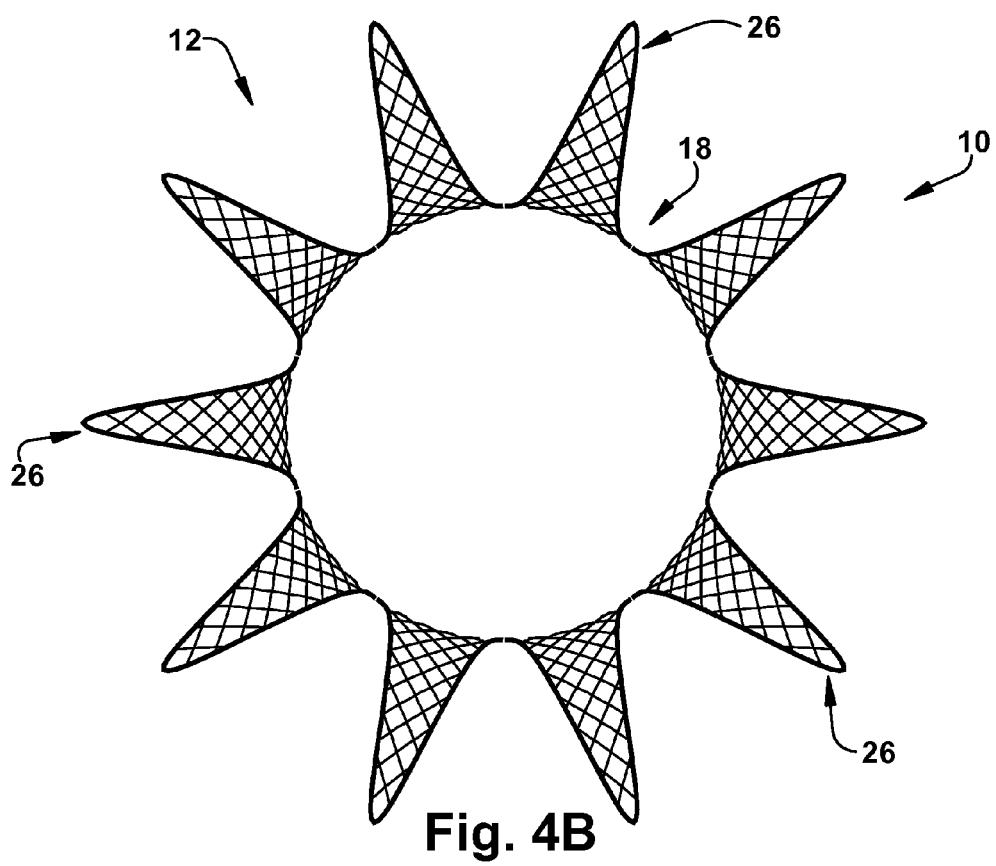

APPARATUS AND METHOD FOR TREATING CARDIOVASCULAR DISEASES

RELATED APPLICATIONS

This application is a continuation-in-part of U.S. patent application Ser. No. 11/789,827, filed Apr. 26, 2007, which claims priority from U.S. Provisional Patent Application Ser. No. 60/795,256, filed on Apr. 26, 2006. The subject matter of the aforementioned applications is hereby incorporated herein by reference in their entireties.

FIELD OF THE INVENTION

The present invention relates to the treatment of cardiovascular diseases, and more particularly relates to an apparatus and method for treating cardiac conditions, such as arrhythmias, heart failure, acute and chronic heart transplant rejection, and pulmonary arterial hypertension.

BACKGROUND OF THE INVENTION

The heart is, in essence, a pump that is responsible for circulating blood throughout the body. In a normally functioning heart, such circulation is caused by the generation of electrical impulses that, for example, increase or decrease the heart rate and/or the force of contraction in response to the demands of the circulatory system. If the electrical signal becomes disturbed in some way, the efficient pumping action of the heart may deteriorate, or even stop altogether.

Disturbance in the regular rhythmic beating of the heart is a common disorder seen in heart disease. Irregular rhythms (arrhythmia) can be a minor annoyance, or may indicate a serious problem. For example, arrhythmias may indicate an underlying abnormality of the heart muscle, valves or arteries, and includes the situation where the heart is beating too slowly (bradycardia) and also where the heart is beating too rapidly (tachycardia).

One particular type of cardiac arrhythmia, known as atrial fibrillation (AF), is a common cardiac rhythm disorder which can affect the quality of a patient's life and may be associated with significant morbidity. Atrial fibrillation is characterized by a rapid disorganized rhythm of the upper chambers of the heart (the atria). Instead of a single wavefront of electrical activation during regular rhythm, AF consists of multiple coexistent wavefronts with random re-entry. The condition may happen by itself (lone AF), may be related with hypertension, valvular disease, or may arise following cardiac surgery.

The etiology of AF is varied and has been hypothesized in some cases to have a genetic component. While medication is effective to control AF in some patients, other primary treatment modalities, such as endocardial ablation or surgical intervention, are often necessary for effective treatment. For example, endovascular approaches may be used to create lesions using an ablation catheter to block intra-atrial conduction. Such primary treatments are not always satisfactory, however, as arrhythmias often reoccur in patients (20-50%) and ablation procedures may sometimes result in unwanted sequelae, such as pulmonary vein stenosis or drug inefficiency or side effects from the complementary pharmacological treatment, and thus additional secondary treatments such as additional ablation procedures may be necessary.

Another cause of significant morbidity and mortality is pulmonary arterial hypertension (PAH). PAH is a disease defined by a progressive elevation of pulmonary artery pressure and pulmonary vascular resistance, leading to right ventricular failure and death. Current therapies for PAH typically involve PDE-5 inhibitors, prostacyclins, endothelin receptor antagonists, and other agents for treating PAH. Such therapies have several drawbacks, however, including drug resistance, non-specific delivery to the pulmonary vasculature, and undesirable side effects.

SUMMARY OF THE INVENTION

In accordance with one aspect of the present invention, a method is provided for treating a cardiovascular disease, such as heart failure or an arrhythmia. One step of the method includes providing an apparatus. The apparatus includes an expandable support member having oppositely disposed proximal and distal end portions and a main body portion extending between the end portions. The proximal end portion includes a plurality of wing members extending from the main body portion. At least a portion of the expandable support member is treated with at least one therapeutic agent for elution into a blood vessel. The expandable support member is inserted into the pulmonary vasculature and then advanced to a bifurcation in the pulmonary vasculature. The bifurcation includes the intersection of a first pulmonary vessel, a second pulmonary vessel, and a third pulmonary vessel. The expandable support member is secured at the bifurcation to treat pulmonary arterial hypertension (PAH), for example, or to treat other etiologies or causes of pulmonary hypertension.

In accordance with another aspect of the present invention, a method is provided for treating a cardiovascular disease. One step of the method includes providing an apparatus comprising an expandable support member having oppositely disposed proximal and distal end portions and a main body portion extending between the end portions. The proximal end portion comprises a plurality of wing members extending from the main body portion. At least a portion of the expandable support member is treated with at least one therapeutic agent for elution into an atrial chamber and/or cardiac tissue. The expandable support member can be inserted into an atrial appendage. The atrial appendage has an ostium surrounded by an antrum of the atrial chamber. Next, the expandable support member is secured in the atrial appendage. The at least one therapeutic agent can elute into the atrial chamber and/or cardiac tissue when treating a cardiovascular disease, such as an arrhythmia.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 4A is a cross-sectional view of the apparatus shown in FIG. 1A;

FIG. 4B is a plan view of the apparatus shown in FIG. 1A;

DETAILED DESCRIPTION OF EMBODIMENTS

Figure 1:
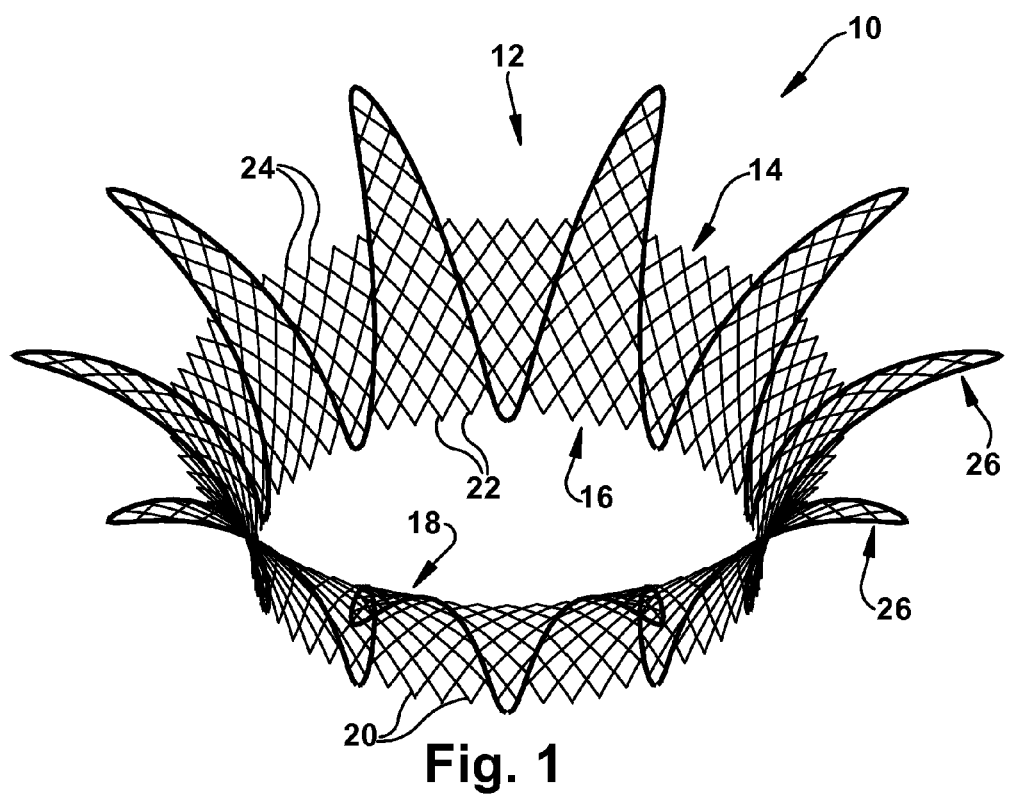
FIG. 1A is a perspective view showing an apparatus, in an expanded configuration, for treating cardiovascular diseases constructed in accordance with the present invention.
FIG. 1B is a perspective view showing an alternative embodiment of the apparatus in FIG. 1A.
FIG. 1C is a perspective view showing an alternative embodiment of the apparatus in FIG. 1B.

The present invention relates to the treatment of cardiovascular diseases, and more specifically relates to an apparatus and method for treating cardiac conditions, such as heart failure, arrhythmias, acute and chronic heart transplant rejection, and pulmonary arterial hypertension. As representative of the present invention, FIG. 1A illustrates an apparatus 10 for treating cardiac arrhythmias, such as atrial fibrillation (AF). It should be understood, however, that the apparatus 10 disclosed herein may be used to treat other cardiac arrhythmias including, but not limited to, premature atrial contraction, atrial flutter, supraventricular tachycardia, sick sinus syndrome, atrioventricular block, ventricular fibrillation, premature ventricular contraction, ventricular tachycardia, and other cardiovascular diseases such as heart failure, acute and chronic heart transplant rejection, and pulmonary arterial hypertension. Further, it is contemplated that the apparatus 10 may also be useful as a complimentary treatment to pacemaker implantation and/or defibrillator implantation.

Figure 2:
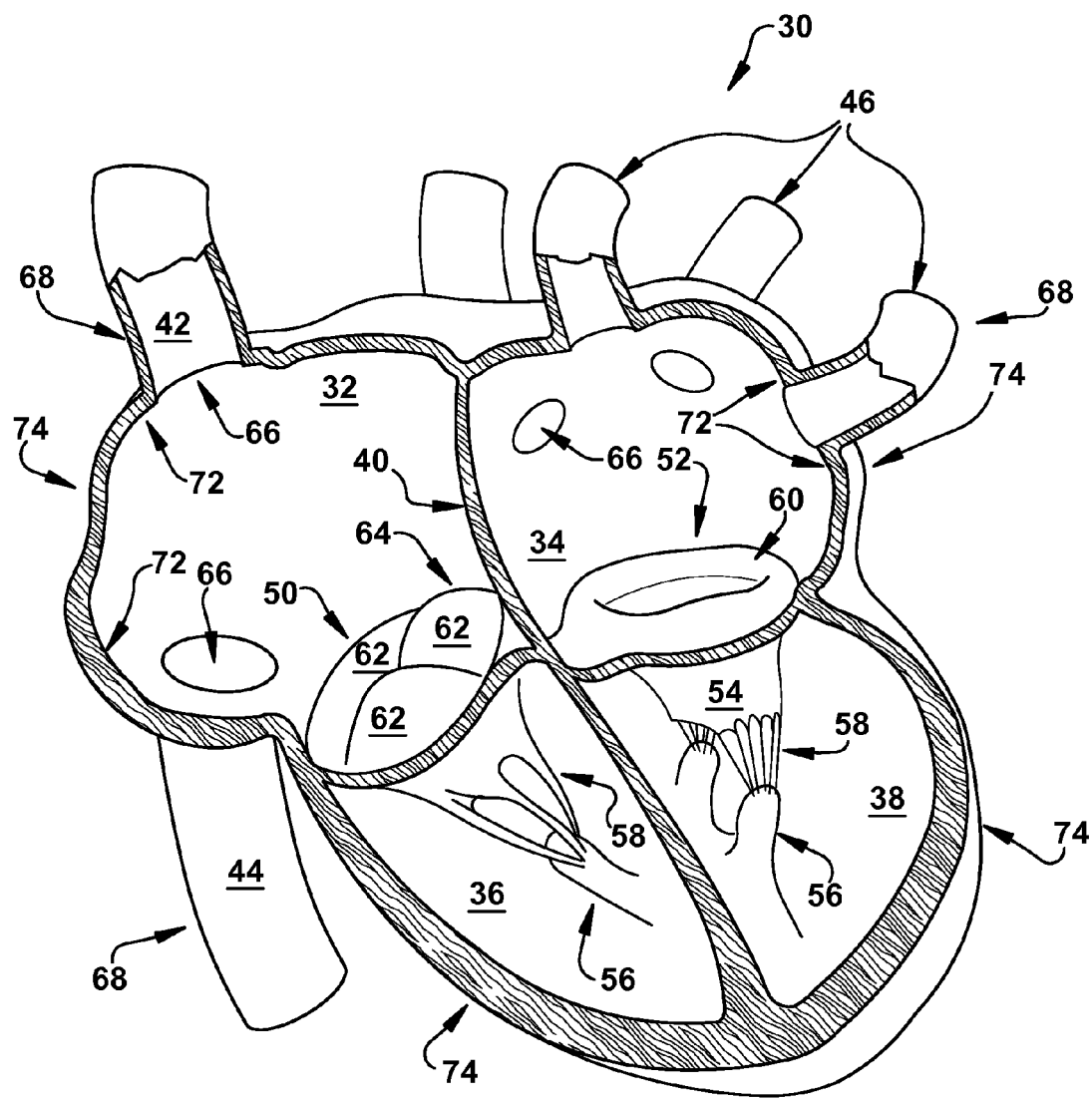
FIG. 2 is a cross-sectional schematic view of a human heart.
Figure 2A:
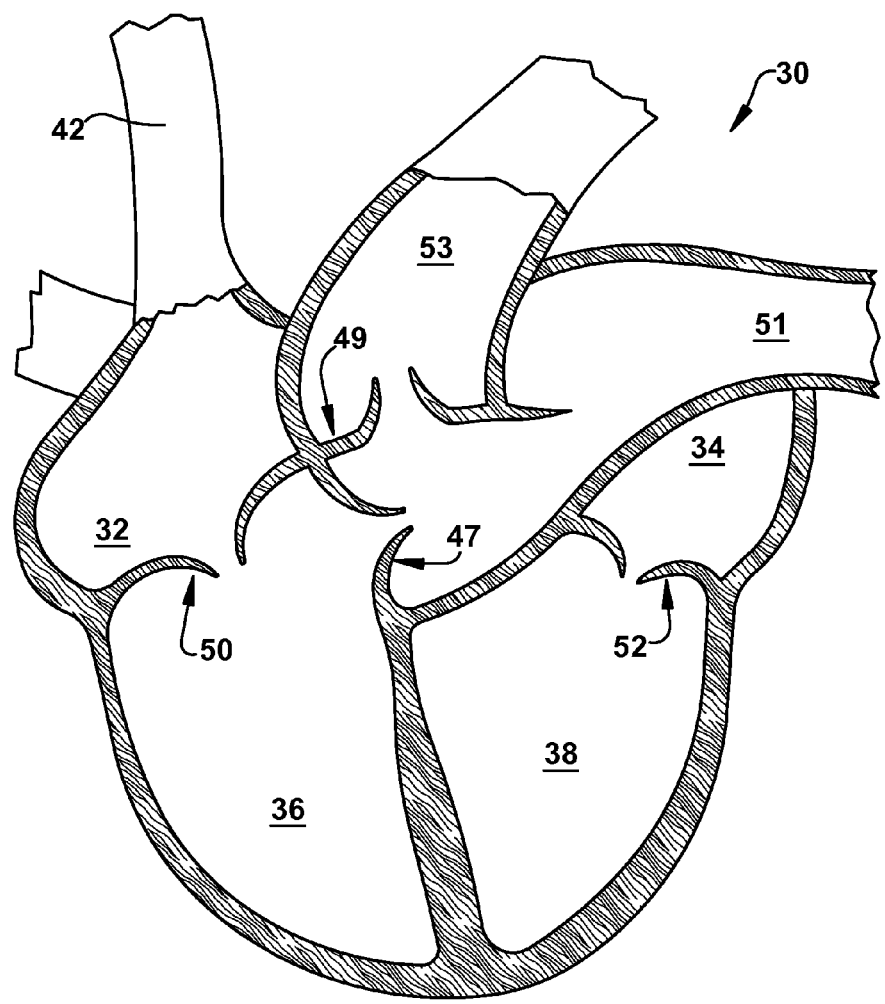
FIG. 2A is different cross-sectional schematic view of the human heart shown in FIG. 2.

FIG. 2 schematically illustrates a human heart 30 which includes four chambers: the right and left atria 32 and 34, and the right and left ventricles 36 and 38, respectively. The right and left atria 32 and 34 are divided by the interatrial septum 40. The thin-walled right atrium 32 receives deoxygenated blood from the superior vena cava 42, the inferior vena cava 44, and from the coronary sinus (not shown). The thin-walled left atrium 34 receives oxygenated blood from pulmonary veins 46. The right and left ventricles 36 and 38 pump deoxygenated and oxygenated blood, respectively, the right ventricle to the pulmonary circuit and the left ventricle throughout the body, and the pocket-like semilunar pulmonary valve 47 (FIG. 2A) and aortic valve 49 prevent reflux into the ventricles. Atrial blood is pumped through the atrioventricular orifices, guarded by the tri-leaflet tricuspid valve 50 (FIGS. 2 and 2A) on the right side of the heart 36 and the bi-leaflet mitral valve 52 on the left side of the heart, while ventricular blood is pumped through the pulmonary artery 51 (FIG. 2A) and the aorta 53 (FIG. 2A). The leaflets 54 (FIG. 2) of the mitral valve 52 are attached to the papillary muscles 56 in the left ventricle 38 by chordae tendineae 58. The leaflets 54 of the mitral valve 52 extend across an annulus 60, which is an area of heart wall tissue at the junction of the atrial and ventricular walls that is relatively fibrous and significantly stronger than leaflet tissue. Similarly, the leaflets 62 of the tricuspid valve 50 are attached to the papillary muscles 56 in the right ventricle 36 by chordae tendineae 58. The leaflets 62 of the tricuspid valve 50 extend across an annulus 64 (not shown in detail) at the junction of the atrial and ventricular walls.

As shown in FIG. 1A, the present invention comprises an expandable support member 12 having oppositely disposed proximal and distal end portions 14 and 16 and a main body portion 18 extending between the end portions. The expandable support member 12 is both flexible and resilient, and, as discussed in more detail below, can be made of a shape memory material such as Nitinol, stainless steel, or other suitable medical grade metals or plastics (e.g., poly(cyclohexane-1,4-diylacetone dimethylene ketal) and Polyzene-F) having shape memory characteristics. Additionally, all or only a portion of the expandable support member 12 may be made from a bioabsorbable material including, for example, magnesium alloy, dendrimers, biopolymers, such as thermoplastic starch, polylactides, cellulose, and aliphatic aromatic copolyesters. The expandable support member 12 may also be made of a radio-opaque material or include radio-opaque markers to facilitate fluoroscopic visualization. The flexible and expandable properties of the expandable support member 12 facilitate percutaneous delivery of the expandable support member, while also allowing the expandable support member to conform to a portion of the ostium 66 (FIG. 2) of a blood vessel 68, such as the ostium 70 (FIG. 8) of a pulmonary vein 46.

Figure 3:
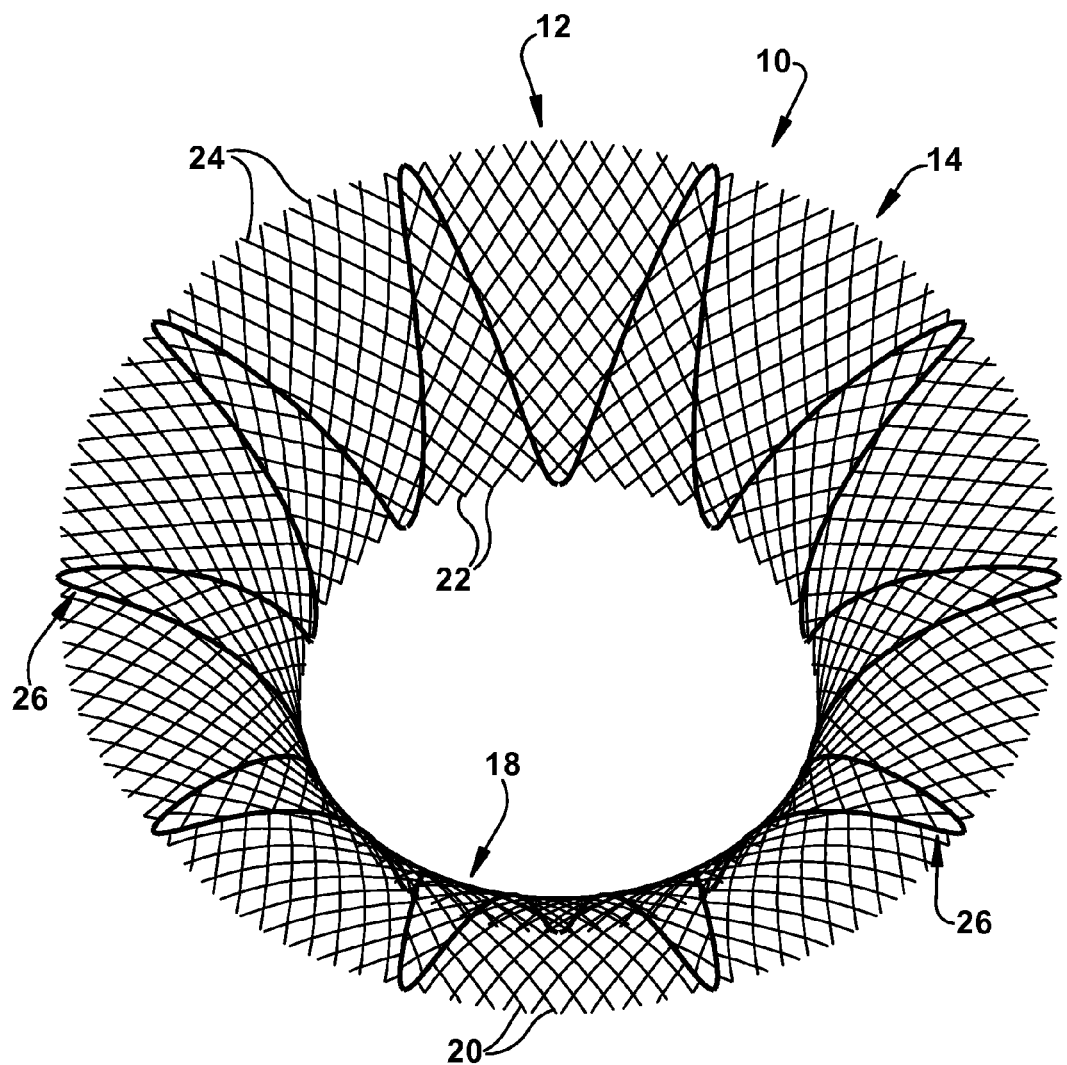
FIG. 3 is a perspective view showing an alternate embodiment of the apparatus in FIG. 1A.

The expandable support member 12 (FIG. 1A) comprises a continuous series of W-shaped segments 20 collectively forming a mesh-like configuration. It is contemplated, however, that other geometries may be used. The lower tips 22, as viewed in FIG. 1A, of the W-shaped segments 20 form the distal end portion 16 of the expandable support member 12, and the upper tips 24 of the W-shaped segments form the proximal end portion 14 of the expandable support member. As shown in FIG. 1A, for example, both the wing members 26 and the main body portion 18 of the expandable support member 12 may have a mesh-like configuration. Alternatively, the entire length L (FIG. 4A) of the main body portion 18, including the wing members 26, may have a mesh-like configuration as illustrated in FIG. 3.

Referring to FIGS. 4A and 4B, the main body portion 18 of the expandable support member 12 is defined between the proximal and distal end portions 14 and 16. The main body portion 18 has a generally cylindrical shape and is adapted to conform to the three-dimensional shape of a blood vessel 68 (FIG. 2). The main body portion 18 (FIG. 4A) may also have a conical shape, depending on the geometry of the blood vessel 68 (FIG. 2). The size of the main body portion 18 (FIG. 4B) may be varied as needed. For example, the circumference and/or diameter of the main body portion 18 may be varied so that the expandable support member 12 more readily conforms to the shape of the blood vessel 68 (FIG. 2). Additionally or optionally, the length L' (FIG. 4A) of the main body portion 18 may also be increased or decreased as needed.

Figure 5:
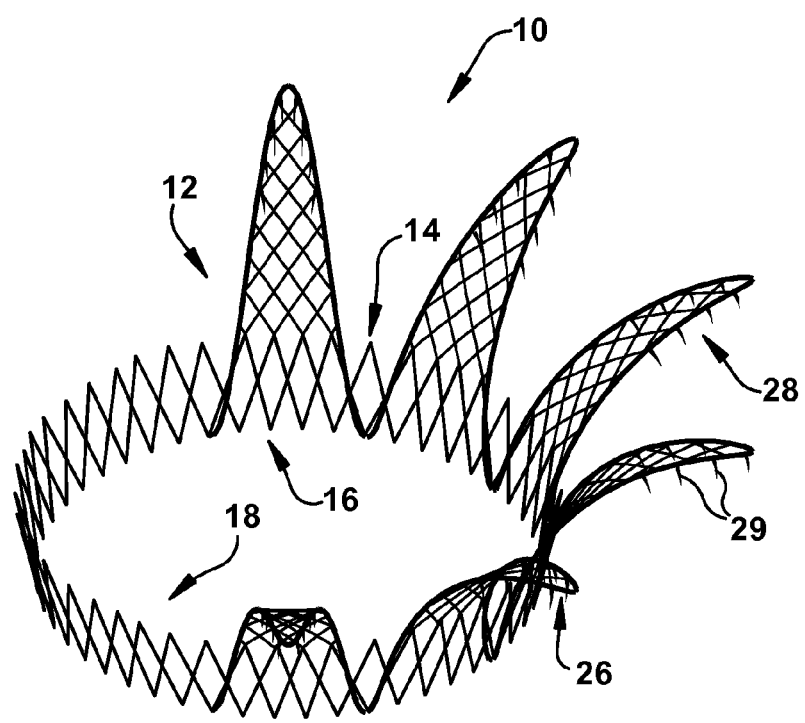
FIG. 5 is a perspective view showing an alternative embodiment of the apparatus in FIG. 1A.

The proximal end portion 14 of the expandable support member 12 comprises a plurality of wing members 26 that resemble arches and which extend integrally from the main body portion 18 generally in the proximal direction. In the embodiment illustrated in FIG. 1A, there are eleven wing members 26 spaced about the circumference of the proximal end portion 14, but it should be understood that more or less than eleven wing members may be used. As shown in FIG. 5, for example, there may be six wing members 26 spaced about the circumference of the proximal end portion 14. The apparatus 10 shown in FIG. 5 may be useful for matching the vascular anatomy. For example, the apparatus 10 may be implanted into the ostium of a superior vena cava 42, as shown in FIGS. 2 and 2A, where a portion of the right atrium wall is nearly flush with the lumen of the superior vena cava.

It should be appreciated that both the proximal and distal end portions 14 and 16 of the expandable support member 12 may include a plurality of wing members 26 (FIG. 1B). As shown in FIG. 1C, it will also be appreciated that the length L' of the main body portion 18 can be increased to a desired length to facilitate implantation of the main body portion in a blood vessel 68 or other cardiac structure.

Figure 7:
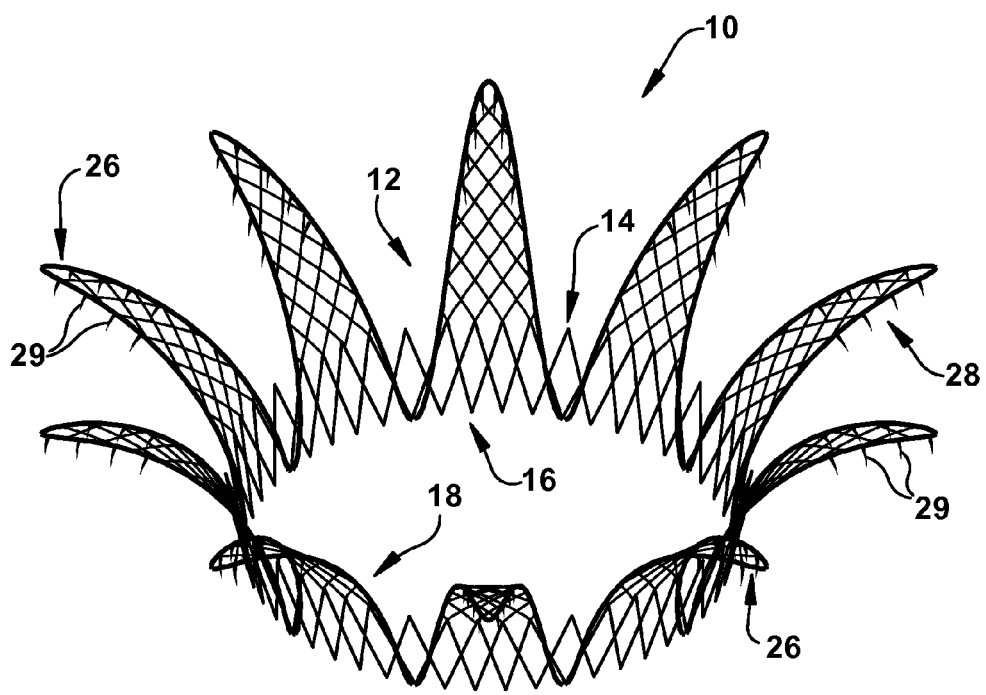
FIG. 7 is a perspective view showing another alternative embodiment of the apparatus in FIG. 1A.

The wing members 26 are shaped for conforming to the shape of an antrum 72 (FIG. 2) of a cardiac chamber 74 surrounding a blood vessel 68. The wing members 26 (FIG. 1A) are resiliently bendable and are movable from the radially collapsed configuration of FIG. 10 (not shown in detail) to the radially expanded condition of FIG. 1A for delivery and placement of the expandable support member 12. Each wing member 26 may also include at least one attachment mechanism 28 (FIG. 7), such as a hook member 29 or barb, for embedding into a cardiac tissue 73 (FIG. 2) of the antrum 72 of a cardiac chamber 74 to help secure the expandable support member 12 (FIG. 1A) in the ostium 66 of a blood vessel 68 (FIG. 2).

At least a portion of the expandable support member 12 (FIG. 1A) is treated with at least one therapeutic agent for elution into a blood vessel 68, a cardiac chamber 74, and/or cardiac wall 73. The therapeutic agent is capable of preventing a variety of pathological conditions including, but not limited to, arrhythmias, thrombosis, stenosis, apoptosis, and inflammation. Accordingly, the therapeutic agent may include at least one of the following: an anti-arrhythmic agent; anticoagulant; an antioxidant; a fibrinolytic; a steroid; an anti-apoptotic agent; an anti-overgrowth agent (i.e., capable of preventing epithelial cell overgrowth); and/or an anti-inflammatory agent. Optionally or additionally, the therapeutic agent may be capable of treating or preventing other disease or disease processes such as microbial infections and heart failure. In these instances, the therapeutic agent may include an anti-microbial agent, an inotropic agent, a chronotropic agent, and/or a biological agent such as a cell or protein. More specific types of these therapeutic agents are listed below, including other types of therapeutic agents not discussed above.

A plurality of portions of the expandable support member 12 (FIG. 1A) may be separately treated with a different one of the therapeutic agents. For example, the main body portion 18 may be treated with an anti-inflammatory agent while each of the wing members 26 is separately treated with an anti-coagulant. Alternatively, each of the wing members 26 may be separately treated with a different therapeutic agent. By treating the expandable support member 12 with different therapeutic agents, cardiac arrhythmias, as well as different medical sequelae associated with primary catheter-based treatments for cardiac arrhythmias, can be simultaneously treated. Implanting the apparatus 10 in a pulmonary vein 46 (FIG. 2) following an ablative surgical intervention, for example, may induce partial or complete mechanical, electrical, and/or pharmaco-biological isolation of dysfunctional electrical impulses emanating from the pulmonary vein by the localized delivery of at least one therapeutic agent to the post-ablative site. It should be appreciated that the expandable support member 12 may be treated with any combination and/or variation of the therapeutic agents mentioned above and discussed further below.

Examples of acceptable therapeutic agents include heparin, synthetic heparin analogues (e.g., fondaparinux), G(GP) $II_b/III_a$ inhibitors, vitronectin receptor antagonists, hirudin, antithrombin III, drotrecogin alpha; fibrinolytics such as alteplase, plasmin, lysokinase, factor XIIa, factor VIIa, prourokinase, urokinase, streptokinase; thrombocyte aggregation inhibitors such as ticlopidine, clopidogrel, abciximab, dextrans; corticosteroids such as aldlometasones, estradiols, such as 17β-estradiol, amcinonides, augmented betamethasones, beclomethasones, betamethasones, budesonides, cortisones, clobetasol, clocortolones, desonides, desoximetasones, dexamethasones, flucinolones, fluocinonides, flurandrenolides, flunisolides, fluticasones, halcinonides, halobetasol, hydrocortisones, methylprednisolones, mometasones, prednicarbates, prednisones, prednisolones, triamcinolones; fibrinolytic agents such as tissue plasminogen activator, streptokinase, dipyridamole, ticlopidine, clopidine, and abciximab; non-steroidal anti-inflammatory drugs such as salicyclic acid and salicyclic acid derivatives, para-aminophenol derivatives, indole and indene acetic acids (e.g., etodolac, indomethacin, and sulindac), heteroaryl acetic acids (e.g., ketorolac, diclofenac, and tolmetin), arylpropionic acids (e.g., ibuprofen and derivatives thereof), anthranilic acids (e.g., meclofenamates and mefenamic acid), enolic acids (e.g., piroxicam, tenoxicam, phenylbutazone, and oxyphenthatrazone), gold compounds (e.g., auranofin, aurothioglucose, and gold sodium thiomalate), diflunisal, meloxicam, nabumetones, naproxen, oxaprozin, salsalate, celecoxib, rofecoxib; cytostatics such as alkaloids and podophyllum toxins such as vinblastin, vincristin; alkylants such as nitrosoureas and nitrogen lost analogues; cytotoxic antibiotics such as daunorubicin, doxorubicin, and other anthracyclins and related substances, bleomycin, and mitomycin; antimetabolites such as folic acid analogues, purine analogues and related inhibitors (e.g., mercaptopurine, thioguanine, pentostatin, and 2-chlorodeoxyadenosine), pyrimidine analogues (e.g., fluorouracil, floxuridine, and cytarabine), and platinum coordination complexes (e.g., cisplatinum, carboplatinum and oxaliplatinum); tacrolimus, azathioprine, cyclosporine, paclitaxel, docetaxel, sirolimus; amsacrin, irinotecan, imatinib, topotecan, interferon-alpha 2a, interferon-alpha 2b, hydroxycarbamide, miltefosin, pentostatin, porfimer, aldesleukin, bexarotene, and tretinoin; antiandrogens and antiestrogens; antiarrythmics, in particular antiarrhythmics of class I such as antiarrhythmics of the quinidine type (e.g., quinidine, dysopyramide, ajmaline, prajmalium bitartrate, and detajmium bitartrate); antiarrhythmics of the lidocaine type, (e.g., lidocaine, mexiletin, phenyloin, and tocainid); antiarrhythmics of class I C (e.g., propafenone, flecainide (acetate)); antiarrhythmics of class II, including betareceptor blockers such as metoprolol, esmolol, propranolol, metoprolol, atenolol, and oxprenolol; antiarrhythmics of class III such as amiodarone and sotalol; antiarrhythmics of class IV such as diltiazem, and verapamil; and other antiarrhythmics such as adenosine, orciprenaline, TC-912, endothelin antagonists, phosphodiesterase-5 (PDE-5) inhibitors, prostaglandins (e.g., thromboxane, prostacyclin, and prostaglandin D, E and F), ipratropium bromide, and novel antiproliferative agents, such as imatinib (GLEEVEC).

Other types of therapeutic agents may include digitalis glycosides such as acetyl digoxin/methyldigoxin, digitoxin, and digoxin; heart glycosides such as ouabain and proscillaridin; antihypertensives such as centrally effective antiadrenergic substances (e.g., methyldopa and imidazoline receptor agonists); calcium channel blockers of the dihydropyridine type, such as nifedipine and nitrendipine; ACE inhibitors (e.g., quinaprilate, cilazapril, moexipril, trandolapril, spirapril, imidapril, and trandolapril); angiotensin-II-antagonists (e.g., candesartancilexetil, valsartan, telmisartan, olmesartan medoxomil, and eprosartan); peripherally effective alpha-receptor blockers such as prazosin, urapidil, doxazosin, bunazosin, terazosin, and indoramin; vasodilators such as dihydralazine, diisopropyl amine dichloroacetate, minoxidil, and nitropiusside-sodium; other antihypertonics such as indapamide, codergocrin mesilate, dihydroergotoxin methane sulphonate, cicletanin, bosentan, and fluocortisone; phosphodiesterase inhibitors, such as milrinone and enoximone, as well as antihypotonics (e.g., adrenergics and dopaminergic substances such as dobutamine, epinephrine, etilefrine, norfenefrine, norepinephrine, oxilofrine, dopamine, midodrine, pholedrine, and amezinium methyl) and partial adrenoreceptor agonists (e.g., dihydroergotamine); fibronectin, polylysines and ethylene vinyl acetates; and adhesive substances such as cyanoacrylates, beryllium, and silica.

Additional therapeutic agents may also include antibiotics and anti-infectives, such as: β-lactam antibiotics (e.g., β-lactamase-sensitive penicillins, including benzyl penicillins (penicillin G) and phenoxymethylpenicillin (penicillin V)); β-lactamase-resistant penicillins, such as aminopenicillins, which include amoxicillin, ampicillin, and bacampicillin; acylaminopenicillines such as mezlocillin and piperacillin; carboxypenicillines and cephalosporins (e.g., cefazolin, cefuroxim, cefoxitin, cefotiam, cefaclor, cefadroxil, cefalexin, loracarbef, cefixime, cefuroximaxetil, ceftibuten, cefpodoximproxetil, and cefpodoximproxetil); aztreonam, ertapenem, and meropenem; β-lactamase inhibitors such as sulbactam and sultamicillintosilates; tetracyclines such as doxycycline, minocycline, tetracycline, chlorotetracycline, oxytetracycline; aminoglycosides such as gentamicin, neomycin, streptomycin, tobramycin, amikasin, netilmicin, paromomycin, framycetin, and spectinomycin; makrolide antibiotics such as azithromycin, clarithromycin, erythromycin, roxithromycin, spiramycin, and josamycin; lincosamides such as clindamycin and lincomycin; gyrase inhibitors, such as fluoroquinolones, which include ciprofloxacin, ofloxacin, moxifloxacin, norfloxacin, gatifloxacin, enoxacin, fleroxacin, and levofloxacin; quinolones such as pipemidic acid; sulphonamides such as trimethoprim, sulphadiazin, and sulphalene; glycopeptide antibiotics such as vancomycin and teicoplanin; polypeptide antibiotics, such as polymyxins, which include colistin, polymyxin-b, and nitroimidazol derivatives (e.g., metronidazol and tinidazol); aminoquinolones such as chloroquin, mefloquin, and hydroxychloroquin; biguanides such as proguanil; quinine alkaloids and diaminopyrimidines such as pyrimethamine; amphenicols such as chloramphenicol; rifabutin, dapsone, fusidinic acid, fosfomycin, nifuratel, telithromycin, fusafungin, fosfomycin, pentamidindiisethionate, rifampicin, taurolidine, atovaquone, and linezolid; virostatics such as aciclovir, ganciclovir, famciclovir, foscamet, inosine (dimepranol-4-acetamidobenzoate), valganciclovir, valaciclovir, cidofovir, and brivudin; tyrosine kinase inhibitors; anti-apoptotic agents such as caspase inhibitors (e.g., fluoromethylketone peptide derivatives), calpain inhibitors, cathepsin inhibitors, nitric oxide synthase inhibitors, flavonoids, vitamin A, vitamin C, vitamin E, vitamin D, pycnogenol, super oxidedismutase, N-acetyl cysteine, selenium, catechins, alpha lipoic acid, melatonin, glutathione, zinc chelators, calcium chelators, and L-arginine; Coumadin; beta-blockers; diuretics; spirolactone; TC-313; and natural products such as vinca alkaloids (e.g., vinblastine, vincristine and vinorelbine).

As noted above, the therapeutic agent may also include a biological agent. The biological agent may include organic substances such as peptides, proteins, enzymes, carbohydrates (e.g., monosaccharides, oligosaccharides and polysaccharides), lipids, phospholipids, steroids, lipoproteins, glycoproteins, glycolipids, proteoglycans, polynucleotides (e.g., DNA and RNA), antisense polynucleotides (e.g., c-myc antisense), antibodies (e.g., monoclonal or polyclonal) and/or antibody fragments (e.g., anti-CD34 antibody), bioabsorbable polymers (e.g., polylactonic acid), chitosan, extracellular matrix modulators, such as matrix metalloproteinases (MMP), which include MMP-2, MMP-9 and Batimastat; and protease inhibitors.

Biological agents may include, for example, agents capable of stimulating angiogenesis in the myocardium. Such agents may include vascular endothelial growth factor (VEGF), basic fibroblast growth factor (bFGF), non-viral DNA, viral DNA, and endothelial growth factors (e.g., FGF-1, FGF-2, VEGF, TGF). Other growth factors may include erythropoietin and/or various hormones such as corticotropins, gonadotropins, thyrotrophin, desmopressin, terlipressin, oxytocin, cetrorelix, corticorelin, leuprorelin, triptorelin, gonadorelin, ganirelix, buserelin, nafarelin, and goserelin. Additional growth factors may also include cytokines, epidermal growth factors (EGF), platelet derived growth factor (PDGF), transforming growth factors-β (TGF-β), transforming growth factor-α (TGF-α), insulin-like growth factor-I (IGF-I), insulin-like growth factor-II (IGF-II), interleukin-1 (IL-1), interleukin-2 (IL-2), interleukin-6 (IL-6), interleukin-8 (IL-8), tumour necrosis factor-α (TNF-α), tumour necrosis factor-β (TNF-β), interferon-γ (INF-γ), colony stimulating factors (CSFs); monocyte chemotactic protein, and fibroblast stimulating factor 1.

Still other biological agents may include regulatory peptides such as somatostatin and octreotide; bisphosphonates (e.g., risedronates, pamidronates, ibandronates, zoledronic acid, clodronic acid, etidronic acid, alendronic acid, and tiludronic acid); fluorides such as disodium fluorophosphate and sodium fluoride; calcitonin and dihydrotachystyrene; histamine; fibrin or fibrinogen; endothelin-1; angiotensin II; collagens; bromocriptin; methylsergide; methotrexate; carbontetrachloride and thioacetamide.

The present invention may also be treated (i.e., seeded) with other biological agents, such as cells. Suitable cells may include any one or combination of eukaryotic cells. Additionally or optionally, the cells may be capable of producing therapeutic agents and/or genetically engineered to produce therapeutic agents. Suitable cells for use in the present invention include, for example, progenitor cells such as stem cells. The cells may be autologous or allogenic, genetically engineered or non-engineered, and may include, for example, mesenchymal or mesodermal cells, including, but not limited to, endothelial progenitor cells, endothelial cells, and fibroblasts. Mixtures of such cells can also be used.

A variety of ex vivo or in vivo methods can be used to deliver a nucleic acid molecule or molecules, such as a gene or genes, to the cells. For example, the cells can be modified (i.e., genetically engineered) to produce or secrete any one or combination of the above therapeutic agents, including, but not limited to, anticoagulant agents, antiplatelet agents, antifibrinolytic agents, angiogenesis factors, and the like. Ex vivo gene transfer is a process by which cells are removed from the body using well known techniques, genetically manipulated, usually through transduction or transfection of a nucleic acid molecule into the cells in vitro, and then returned to the body for therapeutic purposes. This contrasts with in vivo genetic engineering where a gene transfer vector or a liposome that contains specific genes is administered to a patient resulting in genetic transfer into cells and tissues in the intact patient. Ex vivo and in vivo gene transfer techniques are well known to one of skill in the art.

To treat the present invention with at least one therapeutic agent, a variety of methods, agents, and compositions may be used. For example, the therapeutic agent can be simply linked to the surface of the expandable support member 12, embedded and released from within polymer materials, such as a polymer matrix, or surrounded by and released through a carrier. Several approaches to treating medical devices with therapeutic agents exist. Some therapeutic agents can be loaded directly onto metallic surfaces; however, a coating composition, typically comprised of at least one polymer and at least one therapeutic agent, is usually used to treat drug-eluting devices. The coating composition ensures retention of the therapeutic agent during deployment and modulates elution kinetics of the therapeutic agent. By altering the release kinetics of different therapeutic agents in the same coating composition, distinct phases of a given disease process may be targeted.

The present invention may be treated with a coating composition comprising at least one therapeutic agent and at least one dendrimer, polymer or oligomer material. The dendrimer(s), polymer(s) and/or oligomer(s) may be of various types and from various sources, including natural or synthetic polymers, which are biocompatible, bioabsorbable and useful for controlled release of the therapeutic agent. For example, synthetic polymers can include polyesters, such as polylactic acid, polyglycolic acid, and/or combinations thereof, polyanhydrides, polycaprolactones, polyhydroxybutyrate valerates, and other bioabsorbable polymers or mixtures of copolymers thereof. Natural polymeric materials can include proteins such as collagen, fibrin, elastin, extracellular matrix components, other biologic agents, and/or mixtures thereof.

The polymer material or mixture thereof of the coating composition can be applied with the therapeutic agent on the surface of the present invention and can comprise a single layer. Optionally, multiple layers of the polymer material can be applied to form the coating composition. Multiple layers of the polymer material can also be applied between layers of the therapeutic agent. For example, the polymeric layers may be applied sequentially, with the first layer directly in contact with the uncoated surface of the apparatus and a second layer comprising the therapeutic agent and having one surface in contact with the first layer and the opposite surface in contact with a third layer of polymeric material which is in contact with the surrounding tissue. Additional layers of the polymeric material and therapeutic agent can be added as required.

Alternatively, the coating composition can be applied as multiple layers comprising one or more therapeutic agents surrounded by polymer material. For instance, the coating composition can comprise multiple layers of a single therapeutic agent, one or more therapeutic agents in each layer, and/or differing therapeutic agents in alternating layers. Alternatively, the layers comprising the therapeutic agent can be separated from one another by a layer of polymer material.

The coating composition may further comprise at least one pharmaceutically acceptable polymers and/or pharmaceutically acceptable carriers, for example, non-absorbable polymers, such as ethylene vinyl acetate and methylmethacrylate. The non-absorbable polymer, for example, can aid in further controlling release of the therapeutic agent by increasing the molecular weight of the coating composition and thereby delaying or slowing the rate of release of the therapeutic agent.

The coating composition can be applied to the present invention using standard techniques to cover the entire surface of the apparatus 10, or partially, as a single layer in a dot matrix pattern, for example. The coating composition can be applied using various techniques available in the art, such as dipping, spraying, vapor deposition, an injection-like and/or a dot matrix-like approach. Upon contact of the coating composition with adjacent tissue where implanted, the coating composition can begin to degrade in a controlled manner. As the coating composition degrades, the therapeutic agent is slowly released into adjacent tissue and/or the blood stream, and the therapeutic agent eluted so that the therapeutic agent can have its effect locally and/or downstream.

Where the therapeutic agent comprises a biological agent, such as cells, the biological agent can be coated directly onto the surface of the present invention or, alternatively, they can be incorporated into the polymeric material (e.g., into a polymer matrix). Such biological agents may also be included within at least one microscopic containment vehicle (e.g., a liposome, nanocapsule, nanoparticle, micelle, synthetic phospholipid, gas-dispersion, emulsion, microemulsion, nanosphere, and the like) that can be stimulated to release the biological agent(s) and/or that release the biological agent(s) in a controlled manner. The microscopic containment vehicle can be coated onto the surface of the present invention or incorporated into the polymeric material. Where the biological agent comprises cells, for example, the cells can be induced to produce, activate, and/or release their cellular products (including one or more therapeutic agents) by an external stimulation device (e.g., an electrical impulse).

Alternatively, cells can constitutively release one or more therapeutic agents at a desired level.

Figure 6:
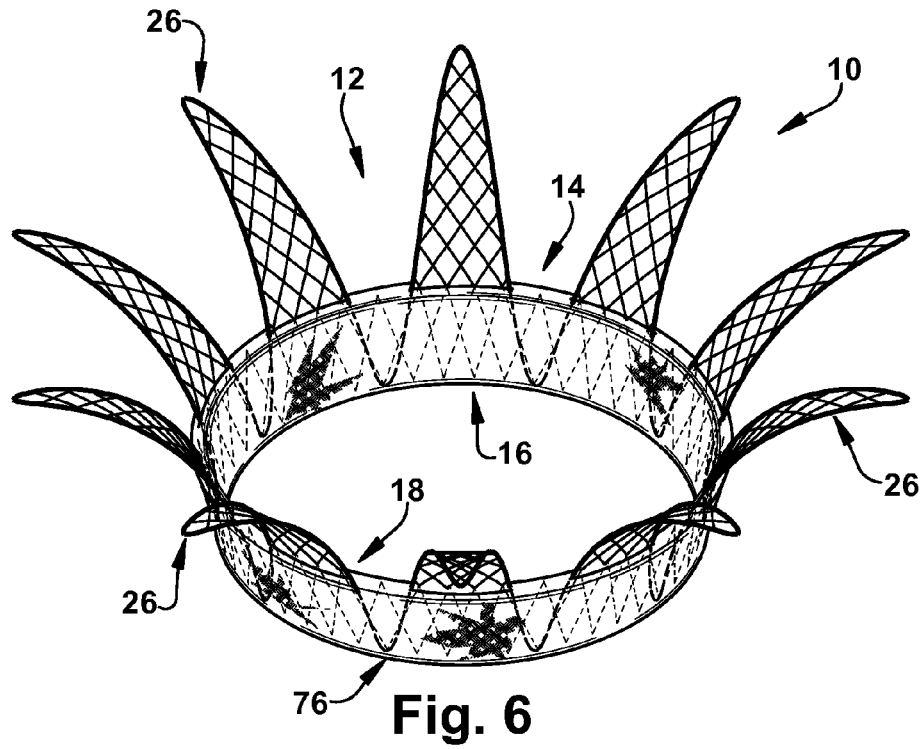
FIG. 6 is a perspective view showing another alternative embodiment of the apparatus in FIG. 1A.

The present invention may further include a layer 76 of biocompatible material covering at least a portion of the expandable support member 12. As shown in FIG. 6, for example, the main body portion 18 may be covered with the layer 76 of biocompatible material. It will be appreciated, however, that the layer 76 of biocompatible material may cover any combination of other portions of the expandable support member 12, such as only the wing members 26 or both the wing members and the main body portion 18.

The layer 76 of biocompatible material may be a synthetic material such as DACRON (Invista, Witchita, Kans.), GORE-TEX (W. L. Gore & Associates, Flagstaff, Ariz.), woven velour, polyurethane, polytetrafluoroethylene (PTFE), expanded PTFE (ePTFE), or heparin-coated fabric. Alternatively, the layer 76 may be a biological material such as bovine or equine pericardium, peritoneal tissue, an allograft, a homograft, patient graft, or a cell-seeded tissue. The layer 76 can cover either the inside surface of the expandable support member 12, the outside surface of the expandable support member, or can be wrapped around both the inside and outside surfaces. The layer 76 may be attached around the entire circumference of the expandable support member 12 or, alternatively, may be attached in pieces or interrupted sections to allow the expandable support member to more easily expand and contract.

The expandable support member 12 may further comprise an electrical mechanism (not shown) for delivering electrical energy to a portion of the ostium 66 (FIG. 2) of a blood vessel 68. The electrical mechanism may comprise, for example, an antenna and a power source coupled to the expandable support member 12 (FIG. 1A), along with an externally located device capable of generating an electrical energy signal. Delivery of electrical energy may be desirable where a conduction block or ablative procedure is needed, for example, and may be achieved by delivering radio frequency energy, microwave energy, laser, ultrasonic energy, freezing (i.e., cryoablation), or any other type of appropriate energy. To select for different capacitive and resistive effects, the expandable support member 12 may be formed from different biocompatible metals such as platinum iridum alloys, ND35N, titanium, Nitinol, and stainless steels. Depending on the construction of the electrical mechanism, the expandable support member 12 may operate by acting as an electrically insulative barrier to an electric signal, a capacitively coupled short across a region of tissue in question, an averager that reduces the effective signal of the region of tissue in question, or any combination of these mechanisms.

As shown in FIGS. 8-12, the present invention may be placed in a patient's pulmonary vein 46 to treat a cardiac disease, such as AF.

Using a percutaneous approach, the patient's left atrium 34 is first accessed. Once the left atrium 34 has been accessed, the dimensions of the pulmonary vein 46, the ostium 70 of the pulmonary vein, and the antrum 72 (FIG. 10) surrounding the ostium are determined. Various devices and methods for determining the dimensions of cardiac and vascular structures are known in the art.

After determining the dimensions of the pulmonary vein 46, the ostium 70 of the pulmonary vein, and the antrum 72, an appropriately-sized apparatus 10 is selected. More particularly, the selected apparatus 10 will be appropriately dimensioned to the size and shape of the pulmonary vein 46, the ostium 70 of the pulmonary vein, and the antrum 72 surrounding the ostium.

Figure 8:
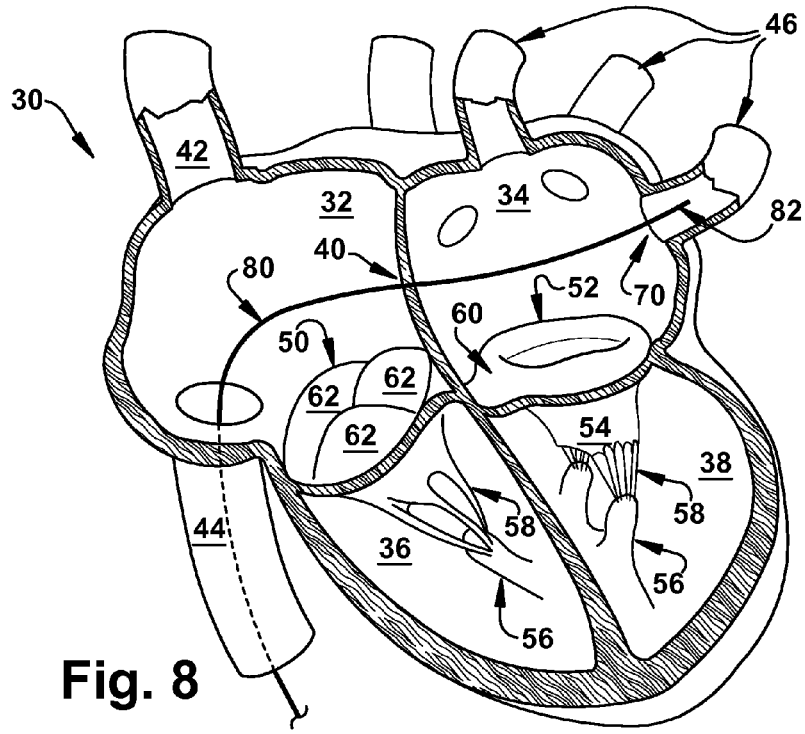
FIG. 8 is a cross-sectional view showing a guidewire extending trans-septally through the human heart.

Next, a guidewire 80 (FIG. 8) is inserted into a femoral vein (not shown) or jugular vein (not shown) and, under image guidance (e.g., fluoroscopy, ultrasound, magnetic resonance, computed tomography, or combinations thereof), respectively steered through the patient's vasculature into the inferior vena cava 44 or superior vena cava 42. The guidewire 80 is then passed across the right atrium 32 so that the distal end 82 of the guidewire pierces the interatrial septum 40 as shown in FIG. 8. The guidewire 80 is then extended across the left atrium 34 and into the pulmonary vein 46 so that the distal end 82 of the guidewire is securely positioned in the pulmonary vein.

In an example of the trans-septal approach, a curved needle (not shown in detail), such as a 70 cm curved Brockenbrough needle (USCI, Billerica, Mass.) and a guidewire 80 (e.g., 0.014 inch PTCA guidewire) can be inserted into the stopcock lumen of the needle with an introducer (not shown) to determine the safety of the guidewire and the needle. For the Inoue technique, a dilator (e.g., a Mullins dilator) (not shown) alone can be advanced to the junction of superior vena cava 42 and right atrium 32 over a guidewire 80 (e.g., a 0.032 inch Terumo J guidewire) from the right femoral vein (not shown). After removing the 0.032 inch Terumo J guidewire, the Brockenbrough needle with a 0.014 inch guidewire can be advanced through the Mullins dilator. To avoid perforation of the dilator wall during needle advancement, the 0.014 inch guidewire can be protruded slightly beyond the tip of the needle and then moved in combination (i.e., the needle-wire combination) through the Mullins dilator. The septal puncture can be performed by pulling the 0.014 inch guidewire slightly below the tip of the needle. The angle of the needle for penetration of the septum 40 can be determined by using dimensions from a previous contrast-enhanced CT scan of the left atrium 34. For example, the CT slice showing the longest length of the atrial septum 40 can be used to determine the angle of the needle. The angle of the needle puncture can then be determined simply as the perpendicular angle of the atrial septum 40.

Figure 9:
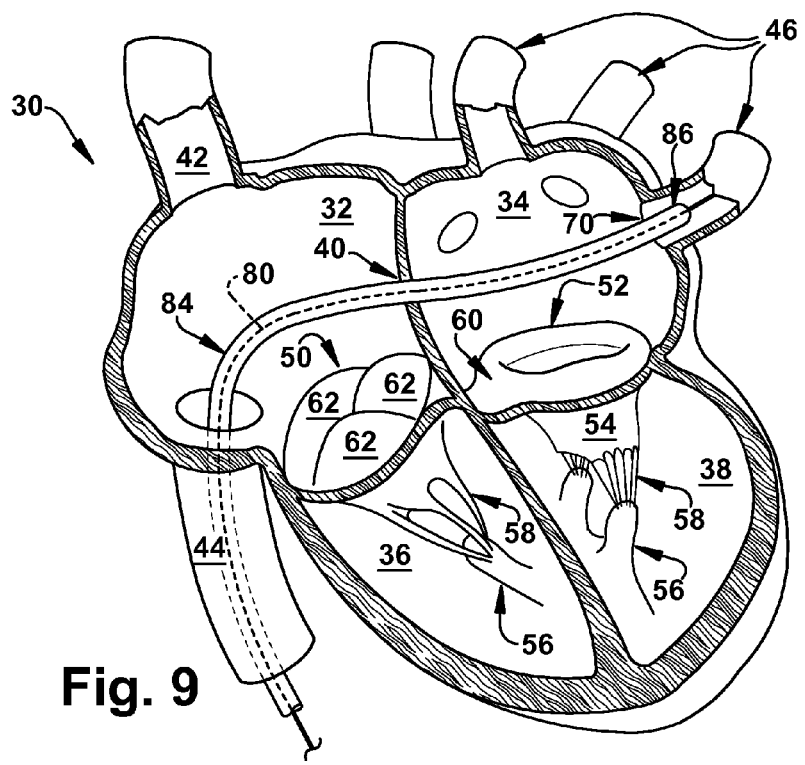
FIG. 9 is a cross-sectional view showing a catheter advanced over the guidewire.

After the guidewire 80 is passed into the pulmonary vein 46, a catheter 84 or sheath is passed over the guidewire as shown in FIG. 9. The catheter 84 may be comprised of a flexible, resiliently yieldable material such as silicone, PTFE, ePTFE, plastic polymer, or the like. The catheter 84 is urged along the guidewire 80 until the distal end 86 of the catheter is appropriately positioned in the ostium 70 of the pulmonary vein 46.

Figure 10:
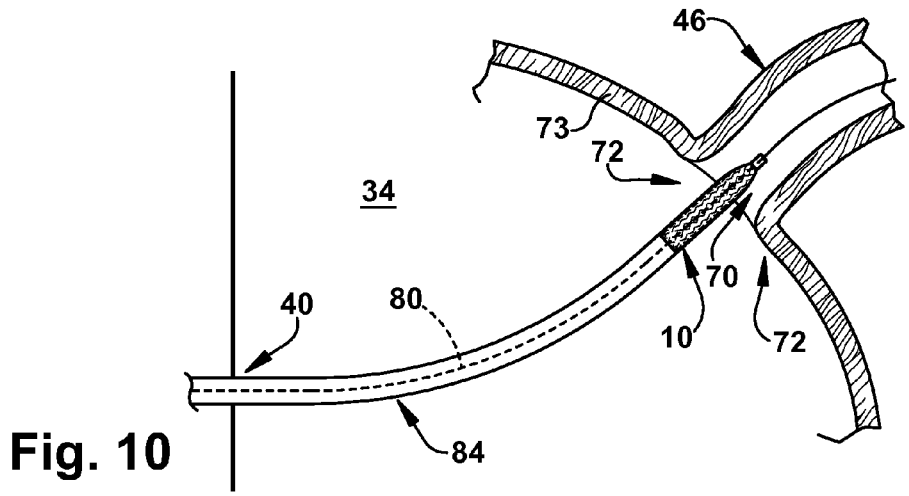
FIG. 10 is a cross-sectional view showing the apparatus in FIG. 1A, in a collapsed configuration, contained in the catheter.
Figure 11:
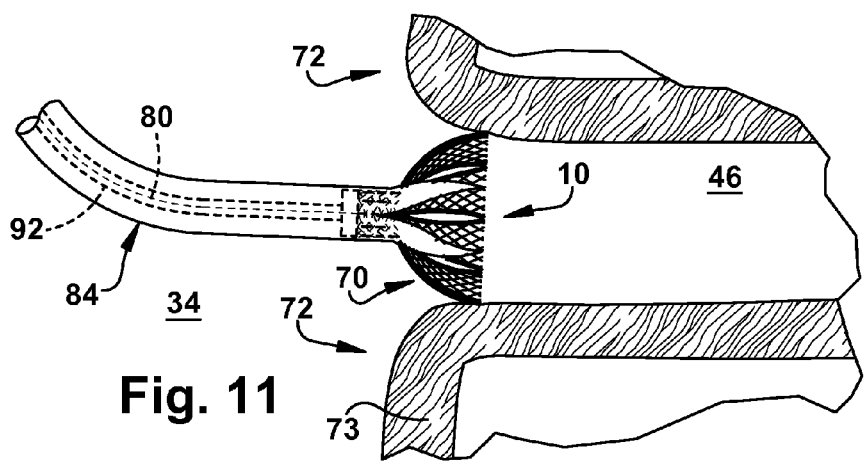
FIG. 11 is a cross-sectional view showing the apparatus of FIG. 1A at an initial stage of delivery in a pulmonary vein.

Next, the apparatus 10, in a collapsed configuration, is attached to a proximal end (not shown) of the guidewire 80, and a pushrod 92 (FIG. 11) or other similar device is then used to urge the apparatus along the guidewire into the left atrium 34 (FIG. 10). When the apparatus 10 is positioned near the distal end 86 of the catheter 84, the catheter is slowly withdrawn. As the catheter 84 is withdrawn, the main body portion 18 of the expandable support member 12 is progressively freed from the catheter and self-expands into the pulmonary vein 46 so that the main body portion engages the wall of the cardiac wall 73 (FIG. 11).

Figure 12:
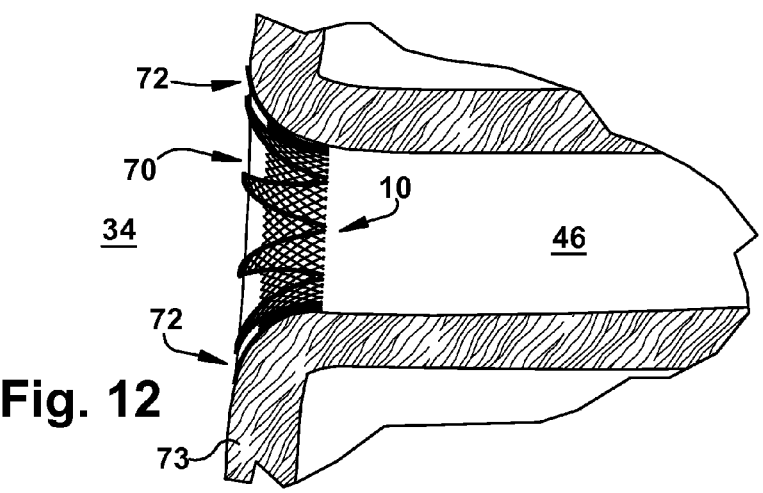
FIG. 12 is a cross-sectional view showing the apparatus of FIG. 1A being deployed in a pulmonary vein.

As the expandable support member 12 is further freed from the catheter 84, each of the wing members 26 expand to their radially expanded configuration. As shown in FIG. 12, each of the wing members 26 expands to engage the antrum 72 surrounding the ostium 70 of the pulmonary vein 46. Where the wing members 26 also comprise the attachment mechanism 28 shown in FIG. 7, the hook members 29 are embedded into the antrum 72 surrounding the ostium 70 of the pulmonary vein 46 and the cardiac wall 73 as the wing members expand into their radially expanded configuration. Once the expandable support member 12 has obtained its expanded configuration, the expandable support member is securely positioned in the ostium 70 of the pulmonary vein 46, and the catheter 84 and guidewire 80 may be withdrawn from the patient. The position of the apparatus 10 may then be varied as needed. For example, the main body portion 18 of the apparatus 10 may be moved either more proximate to, or less proximate from, the ostium 70.

Figure 13:
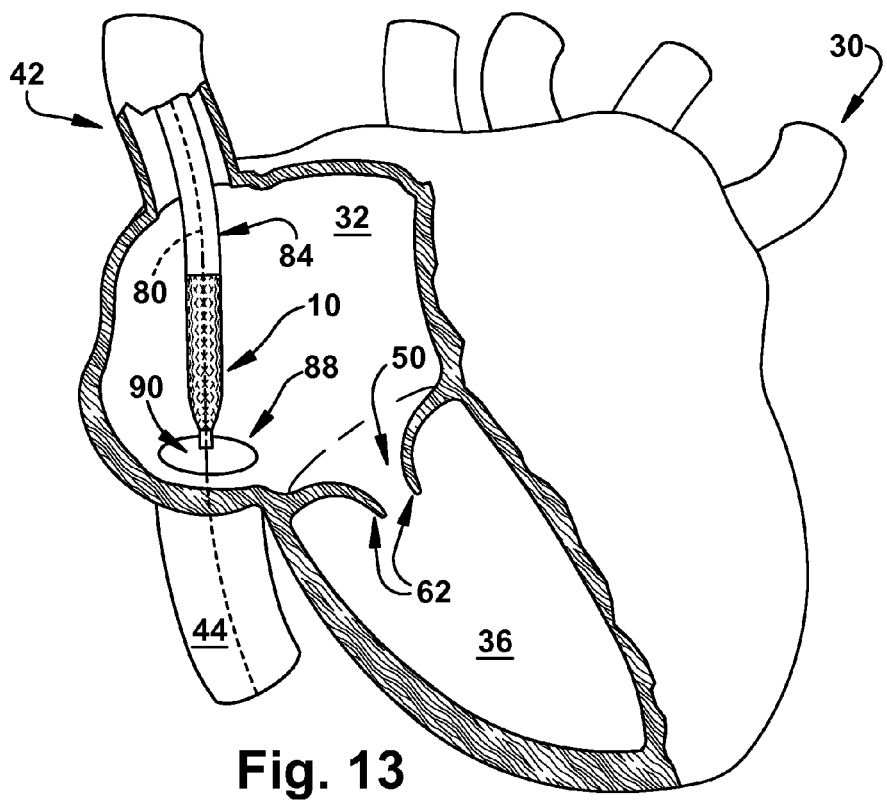
FIG. 13 is a cross-sectional view showing an alternative embodiment of the apparatus in FIG. 1A, in a collapsed configuration, extending into the right atrium of the human heart.
Figure 14:
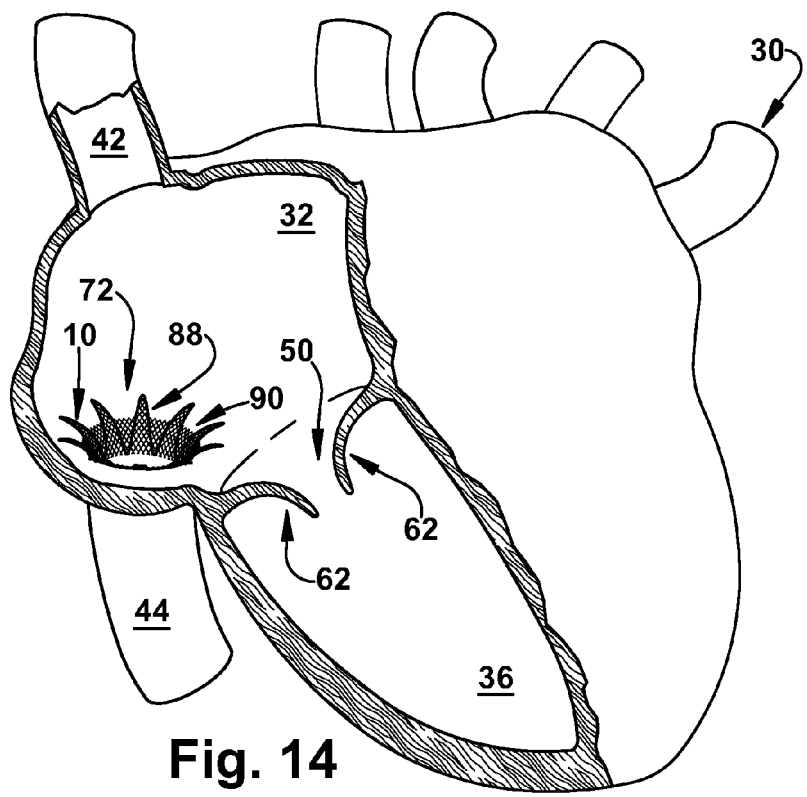
FIG. 14 is a cross-sectional view showing the apparatus in FIG. 13 deployed in the inferior vena cava of the human heart.

In an alternative embodiment of the present invention, the expandable support member 12 may be placed in either the inferior vena cava 44 or the superior vena cava 42. FIGS. 13 and 14 illustrate placement of the apparatus 10 in the inferior vena cava 44.

Using a percutaneous approach, the patient's right atrium 32 may first be accessed. Once the right atrium 32 has been accessed, the dimensions of the inferior vena cava 44, the ostium 90 of the inferior vena cava, and the antrum 72 (FIG. 14) surrounding the inferior vena cava can be determined. Various devices and methods for determining the dimensions of cardiac and vascular structures are known in the art.

After determining the dimensions of the inferior vena cava 44, the ostium 90 of the inferior vena cava, and the antrum 72 surrounding the ostium, an appropriately-sized apparatus 10 is selected. More particularly, the selected apparatus 10 will be appropriately dimensioned to the size and shape of the inferior vena cava 44, the ostium 90 of the inferior vena cava, and the antrum 72 surrounding the ostium.

Next, a guidewire 80 is inserted into the patient's jugular vein (not shown) and, under image guidance (e.g., fluoroscopy, ultrasound, magnetic resonance, computed tomography, or combinations thereof), steered through the superior vena cava 42 into the right atrium 32. Once the guidewire 80 is delivered to the right atrium 32 and secured in the inferior vena cava 44, a catheter 84 or sheath is passed over the guidewire and advanced into the right atrium as shown in FIG. 13. The distal end 86 of the catheter 84 may then be positioned at the ostium 90 of the inferior vena cava 44 and the apparatus 10, in a collapsed configuration, attached to a proximal end (not shown) of the guidewire 80 and then urged into the right atrium 32.

The catheter 84 may then be slowly withdrawn so that the apparatus 10 is progressively freed from the catheter and the main body portion 18 self-expands into the inferior vena cava 44. The catheter 84 may then be withdrawn further so that the wing members 26 are freed from the catheter and move from a collapsed configuration to a radially expanded configuration. As the wing members 26 obtain the radially expanded configuration, the wing members engage the antrum 72 surrounding the ostium 90 of the inferior vena cava 44 (FIG. 14). Consequently, the expandable support member 12 is securely positioned in the ostium 90 of the inferior vena cava 44, and the guidewire 80 and catheter 84 are withdrawn from the patient.

It will be appreciated by one having ordinary skill in the art that the apparatus 10 may implanted using non-percutaneous techniques. For example, an open-chest procedure may be used to implant the apparatus 10 as either a stand alone procedure or as a complement to valve and/or heart transplant surgery. Additionally, it will be appreciated that the apparatus 10 could be implanted either after or during a surgical procedure, such as a CABG.

Figure 15:
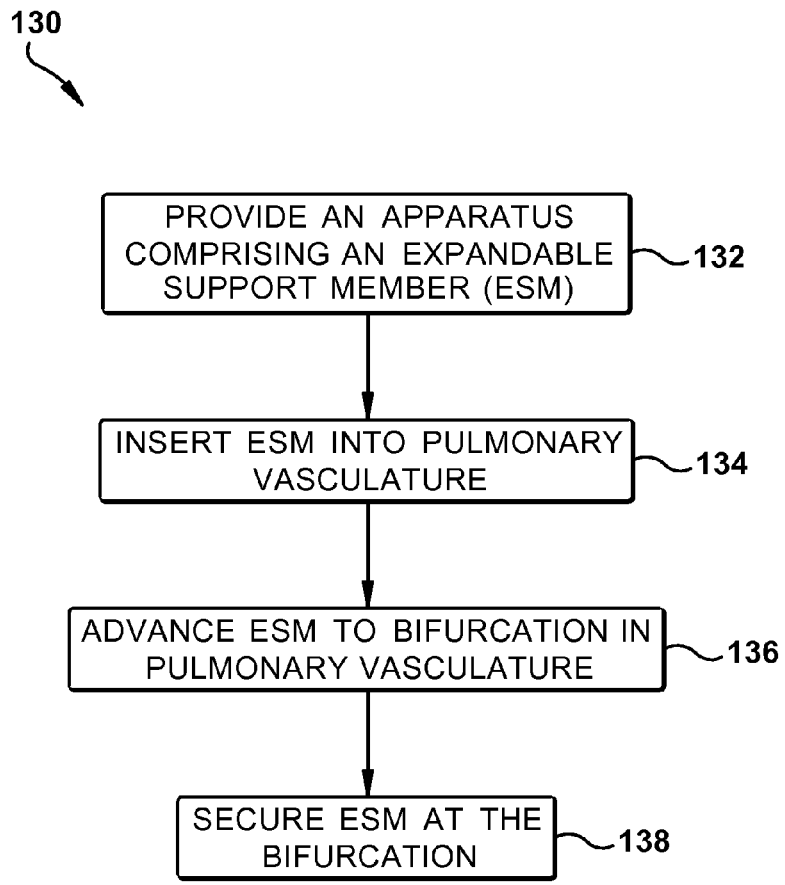
FIG. 15 is a process flow diagram illustrating a method for treating a cardiovascular disease according to another embodiment of the present invention.

FIG. 15 is a process flow diagram illustrating another embodiment of the present invention. In FIG. 15, a method 130 is provided for treating a cardiovascular disease, such as pulmonary arterial hypertension (PAH) in a subject. PAH is characterized by continuous high blood pressure in the pulmonary artery 51 as a result of increased resistance in the pulmonary vasculature. The average blood pressure in a normal pulmonary artery 51 is about 14 mmHg when a subject is resting. In PAH, however, the average blood pressure is usually greater than 25 mmHg. Narrowing of the pulmonary vasculature can cause the right ventricle 36 to work harder to pump blood through the lungs. Over time, the heart muscle weakens and loses its ability to pump enough blood for the body's needs. When this happens, right heart failure can result.

It will be appreciated that the present invention may be used to treat pulmonary hypertension (e.g., PAH) as classified by the Venice 2003 Revised Classification system at the $3^{rd}$ World Symposium on Pulmonary Arterial Hypertension. The Venice 2003 Revised Classification System can be summarized as follows:
- WHO Group I—Pulmonary arterial hypertension;
- WHO Group II—Pulmonary hypertension associated with left heart disease;
- WHO Group III—Pulmonary hypertension associated with lung diseases and/or hypoxemia;
- WHO Group IV—Pulmonary hypertension due to chronic thrombotic and/or embolic disease; and
- WHO Group V—Miscellaneous.

Accordingly, the present invention may be used to treat a subject suffering from PAH according to any one or combination of WHO Groups I-V.

To treat a subject suffering from PAH, for example, one step of the method 130 can include providing an apparatus 10 at 132. The apparatus 10 can be identically or similarly constructed as the apparatus shown in FIGS. 1 and 3-7, as well as other geometries described herein. For example, the apparatus 10 can comprise an expandable support member 12 having oppositely disposed proximal and distal end portions 14 and 16 and a main body portion 18 extending between the end portions. The proximal end portion 14 can comprise a plurality of wing members 26 extending from the main body portion 18. The length L' of the main body portion 18 can be increased, for example, so that the length L' of the main body portion is greater than the length of each of the wing members 26.

It will be appreciated that the expandable support member 12 can have other configurations and/or design modifications to facilitate vascular placement and treatment of cardiovascular diseases. Although not shown, it should be appreciated that both the proximal and distal end portions 14 and 16 of the main body portion 18 can include a plurality of wing members 26.

At least a portion of the expandable support member 12 can be treated with at least one therapeutic agent for eluting into a blood vessel and/or cardiac tissue. For example, each of the wing members 26 can be treated with a PDE-5 inhibitor, such as sildenafil, while the main body portion 18 can be treated with a different agent for treating PAH. Other examples of therapeutic agents that may be used to differentially treat separate portions of the expandable support member 12 are described above.

Figure 16:
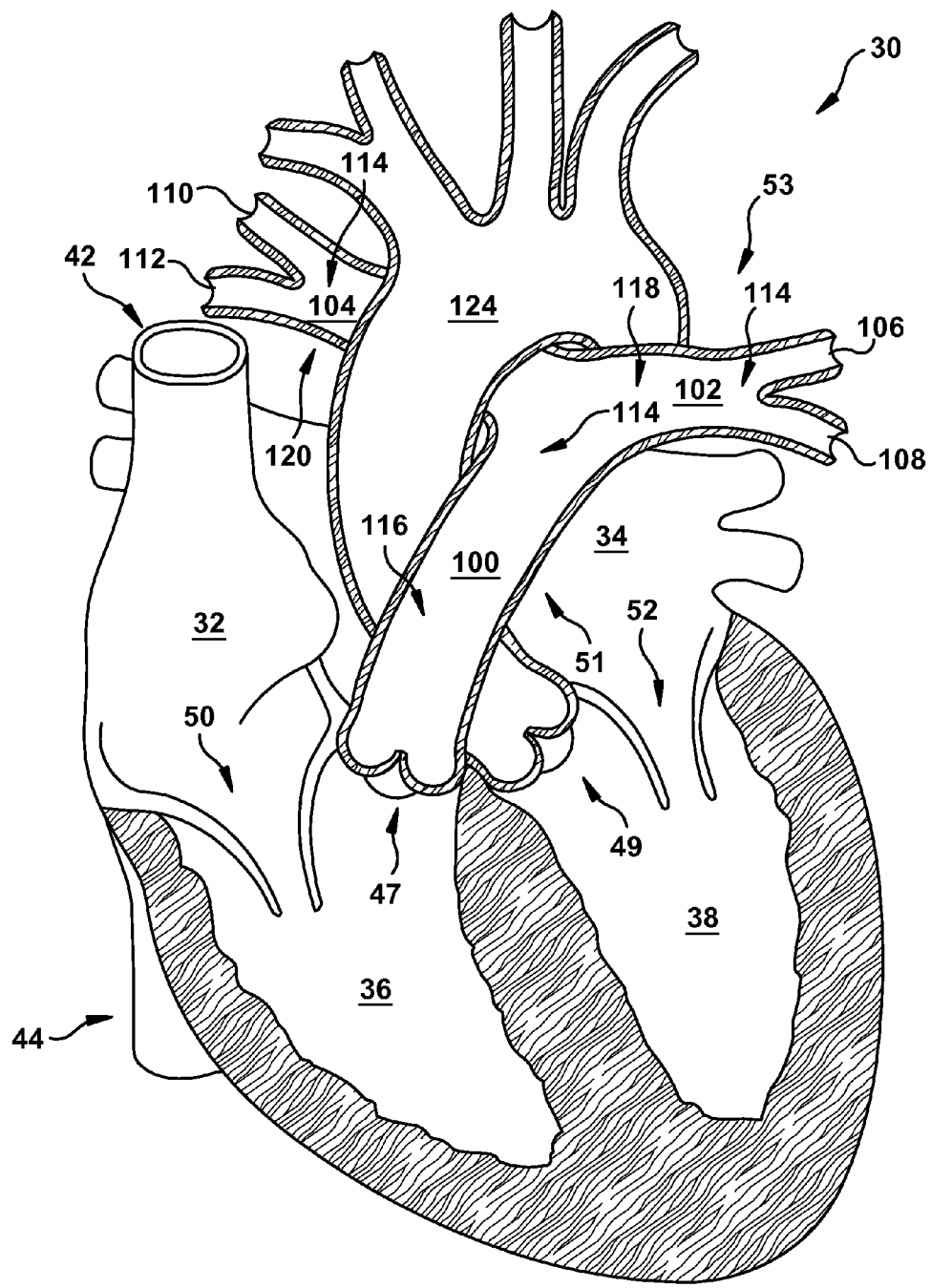
FIG. 16 is a schematic illustration of a human heart.

At 134, the expandable support member 12 can be inserted into the pulmonary vasculature 53 (FIG. 16), such as the pulmonary artery 51 using a percutaneous approach. In the human heart 30, the pulmonary trunk 100 or main pulmonary artery 51 begins at the base of the right ventricle 36. The pulmonary trunk 100 then branches into two pulmonary arteries, the left pulmonary artery 102 and the right pulmonary artery 104. The left pulmonary artery 102 then branches into upper and lower branches 106 and 108. The right pulmonary artery 104 also branches into upper and lower branches 110 and 112. The left and right pulmonary arteries 102 and 104 deliver deoxygenated blood to the corresponding lung.

Prior to inserting the expandable support member 12 into the pulmonary artery 51, an appropriate target site for implantation of the expandable support member can be selected. For example, the target site can comprise a bifurcation 114 in the pulmonary vasculature 53. Generally, the bifurcation 114 can comprise the intersection of a first pulmonary vessel 116, a second pulmonary vessel 118, and a third pulmonary vessel 120. For example, the bifurcation 114 can comprise the intersection of the pulmonary trunk 100, the left pulmonary artery 102, and the right pulmonary artery 104.

The bifurcation 114 can comprise other locations as well, such as the intersection of the left pulmonary artery 102, the upper branch 106 of the left pulmonary artery, and the lower branch 108 of the left pulmonary artery. Additionally, the bifurcation 114 can comprise the intersection of the right pulmonary artery 104, the upper branch 110 of the right pulmonary artery, and the lower branch 112 of the right pulmonary artery.

After identifying a target site, such as the bifurcation 114 located at the intersection of the pulmonary trunk 100, the left pulmonary artery 102, and the right pulmonary artery 104, the dimensions of the bifurcation can be determined. Various devices and methods for determining the dimensions of cardiac vascular structures are known in the art. Once the dimensions of the bifurcation 114 have been determined, an appropriately-sized expandable support member 12 can be selected. More particularly, the selected expandable support member 12 will be appropriately-dimensioned to the size and shape of the bifurcation 114.

Figure 17:
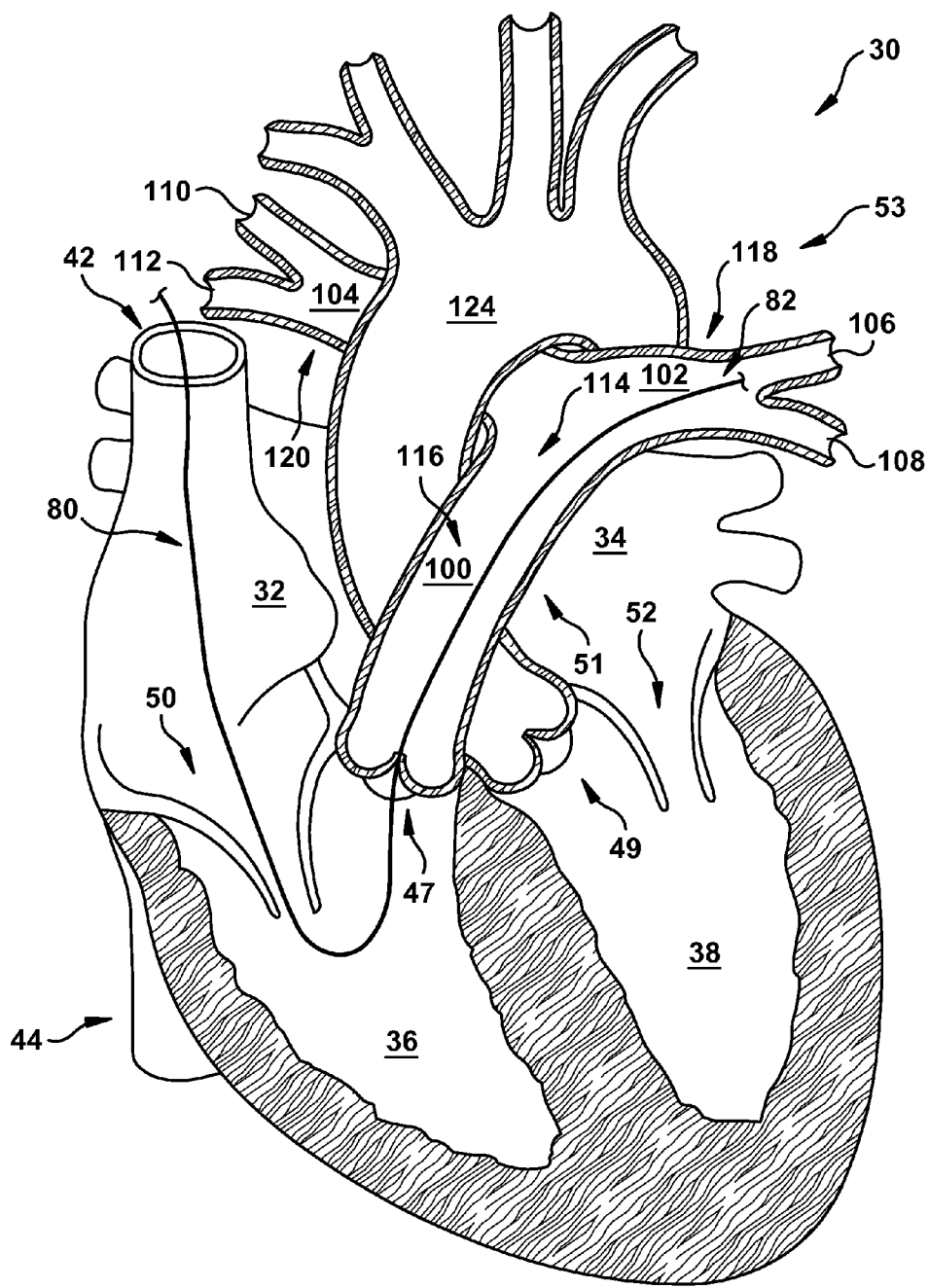
FIG. 17 is a schematic illustration of the heart in FIG. 16 with a guidewire extending through the pulmonary artery.

Next, a guidewire 80 (FIG. 17) can be inserted into a femoral vein (not shown) or a jugular vein (not shown) and, under image guidance (e.g., fluoroscopy, ultrasound, magnetic resonance, computed tomography, or a combination thereof), steered through the subject's vasculature into the inferior vena cava 44 or superior vena cava 42. The guidewire 80 can then be passed across the tricuspid valve 50 and into the right ventricle 36. As shown in FIG. 17, the guidewire can be threaded across the pulmonary valve 47, through the pulmonary trunk 100, and into a portion of the left pulmonary artery 102 so that the distal end 82 of the guidewire is securely positioned therein.

Figure 18:
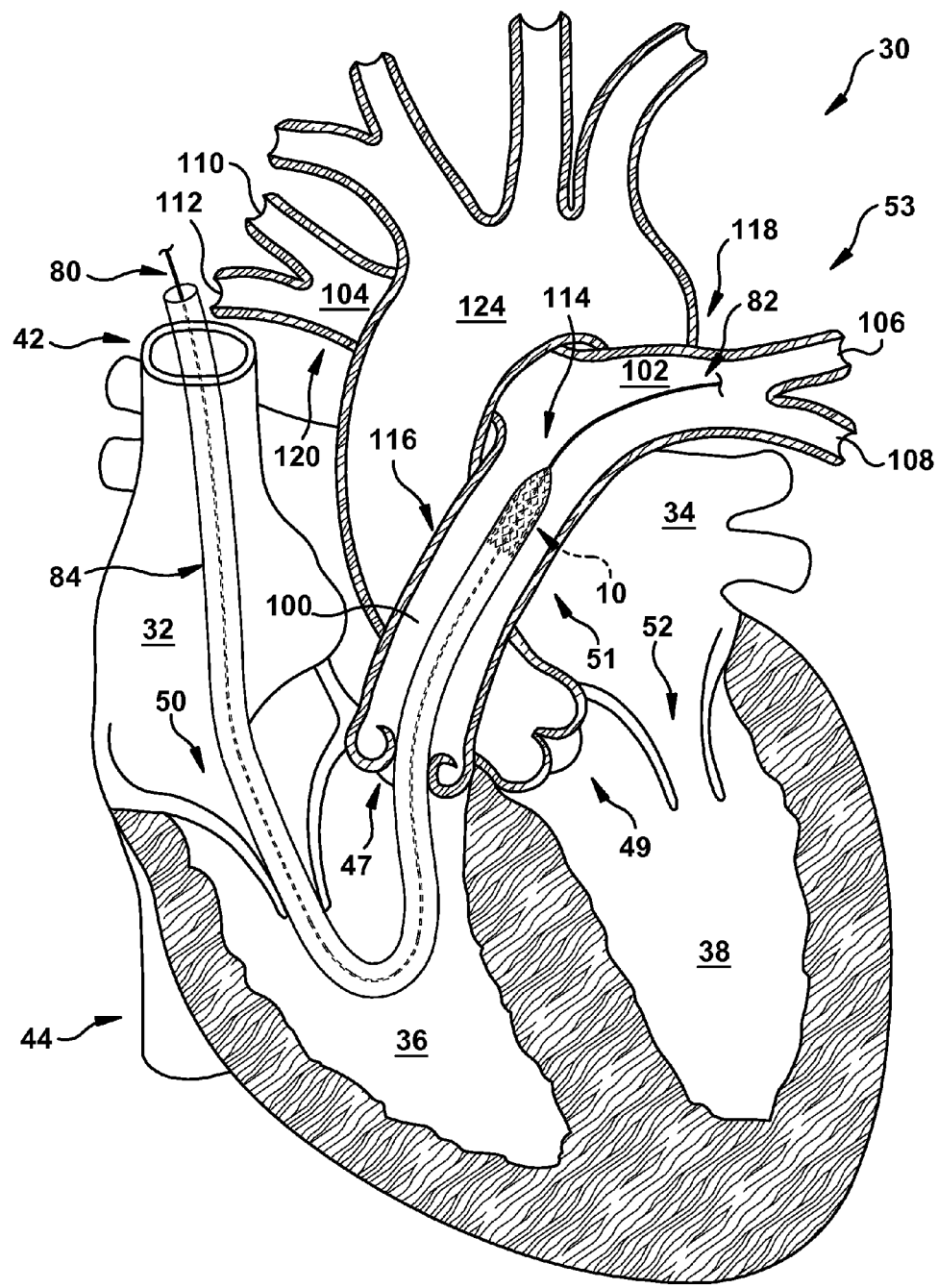
FIG. 18 is a schematic illustration of the heart in FIG. 17 showing the apparatus in FIG. 1A being delivered to a pulmonary arterial bifurcation via a catheter.

After the guidewire 80 has been placed in the pulmonary artery 51, a catheter 84 or sheath can be passed over the guidewire as shown in FIG. 18. The catheter 84 may be comprised of a flexible, resiliently yieldable material such as silicone, PTFE, ePTFE, plastic polymer, or the like. The catheter 84 can be urged along the guidewire 80 until the distal end 82 of the catheter is appropriately positioned at the bifurcation 114.

Figure 19:
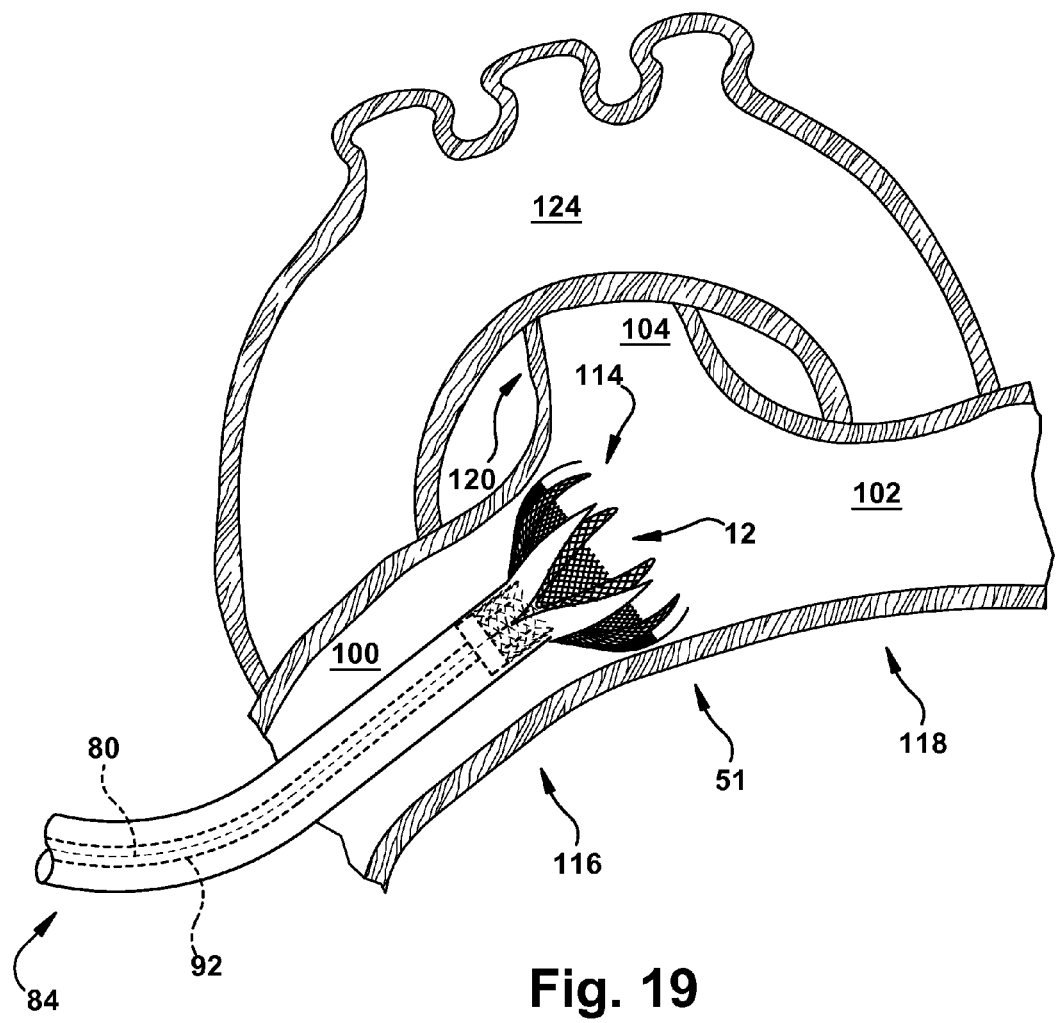
FIG. 19 is a magnified cross-sectional view of the apparatus in FIG. 18 being deployed at the pulmonary arterial bifurcation.

At 136, the expandable support member 12 can be placed into a collapsed configuration, advanced over a proximal end (not shown) of the guidewire 80, and then advanced to the bifurcation 114 using a pushrod 92 (FIG. 19) or other similar device (FIG. 18). Once the expandable support member 12 has been positioned near the distal end 82 of the catheter 84, the catheter can be slowly withdrawn at 138 to secure the expandable support member at the bifurcation 114. As the catheter 84 is withdrawn, the wing members can 26 expand into their radially expanded configuration (FIG. 19) so that the wing members engage a portion of the vessel wall in both the left and right pulmonary arteries 102 and 104.

Figure 20:
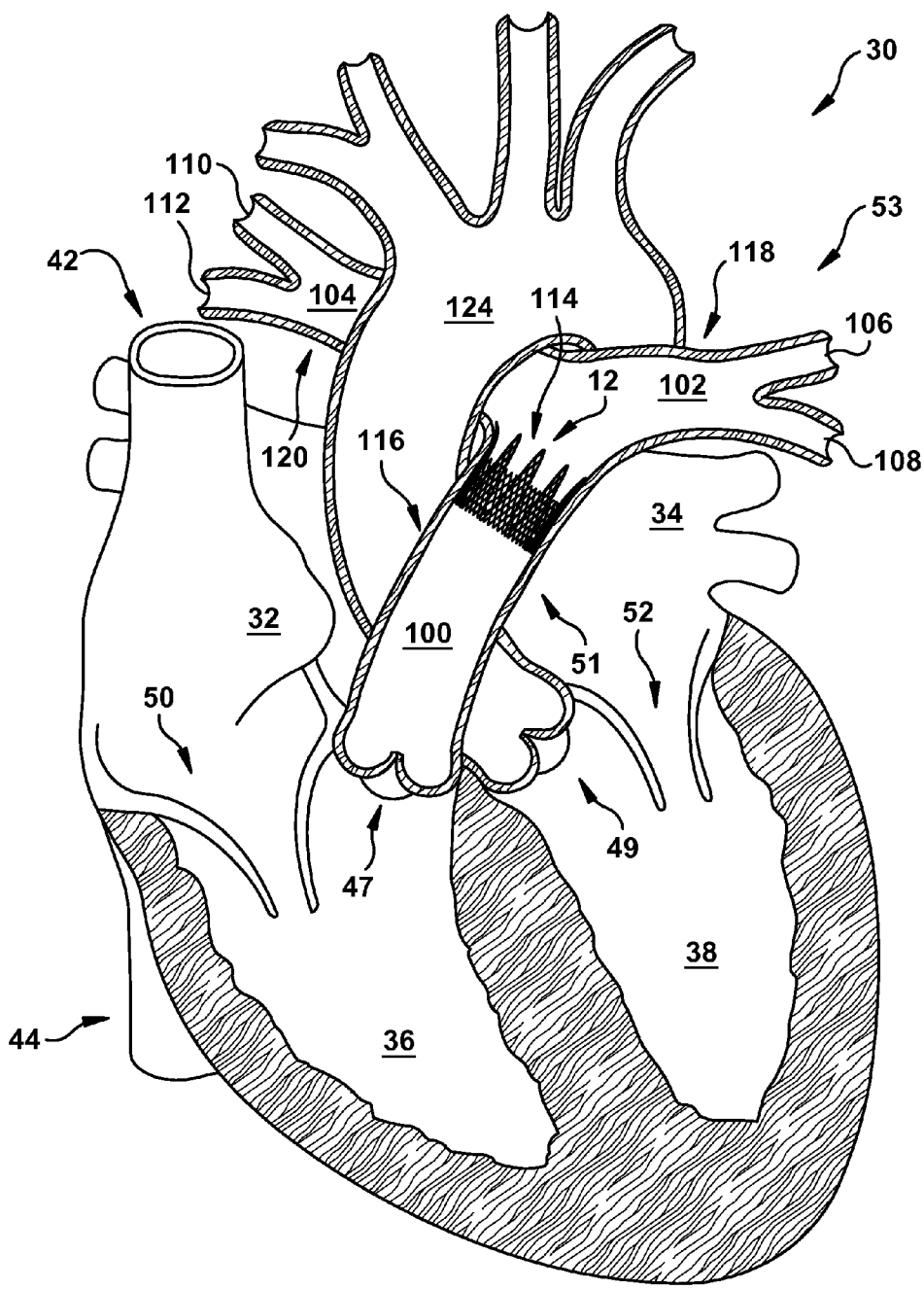
FIG. 20 is a schematic illustration of the heart in FIG. 18 showing the apparatus in FIG. 19 deployed at the pulmonary arterial bifurcation.

As the expandable support member 12 is further freed from the catheter 84, the main body portion 18 can be progressively freed from the catheter and self-expand into contact with the vessel wall of the pulmonary trunk 100 (FIG. 20). Once the expandable support member 12 has obtained its expanded configuration and is securely positioned at the bifurcation 114, the catheter 84 and guidewire 80 may be withdrawn from the subject. With the expandable support member 12 in place, the PDE-5 inhibitor and/or the other agent for treating PAH can begin to elute into the pulmonary vasculature 53 to mitigate the elevated pulmonary blood pressure in the right side of the heart 30.

Figure 21:
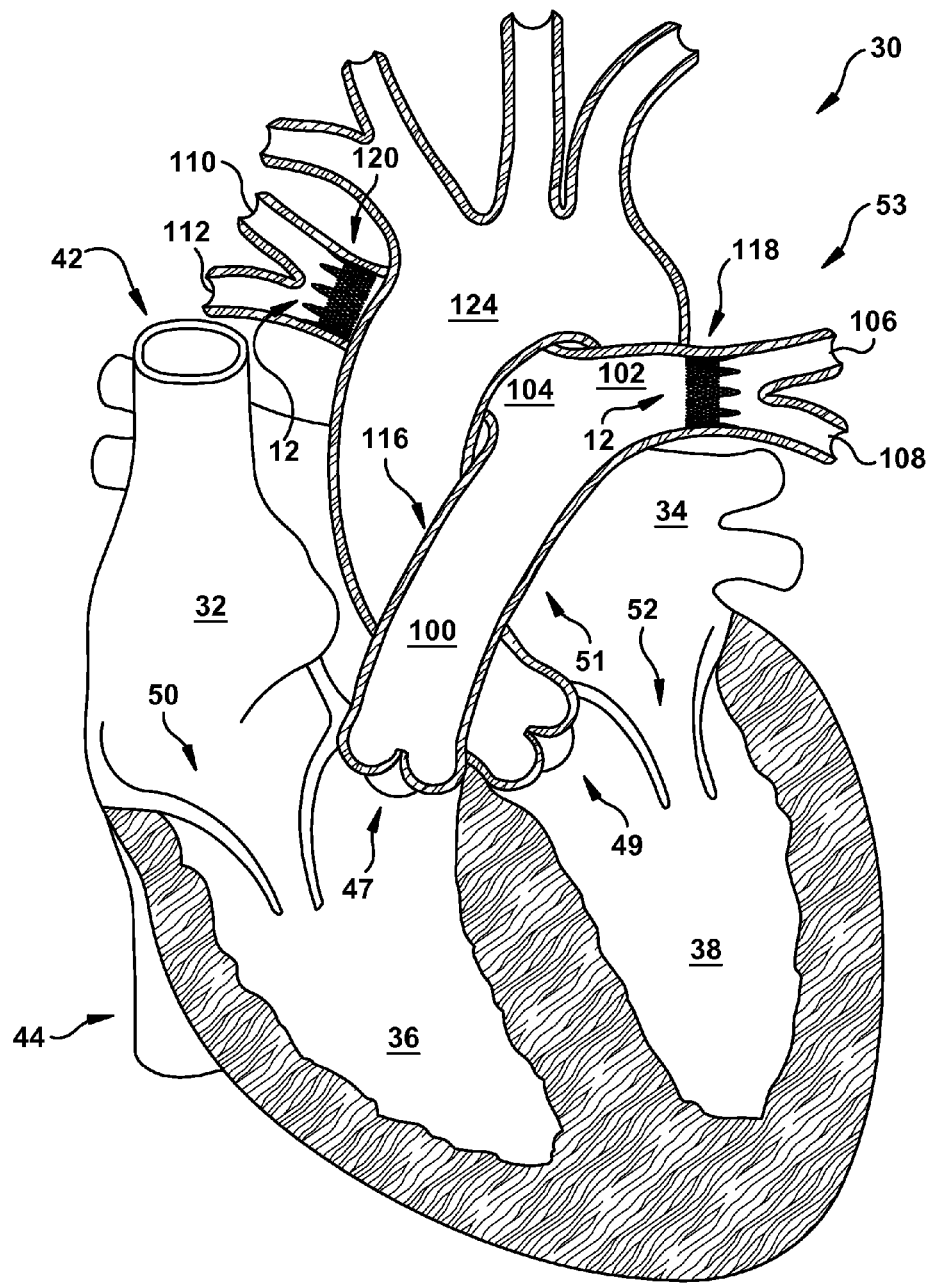
FIG. 21 is a schematic illustration of the human heart in FIG. 16 showing first and second apparatus deployed in the left and right pulmonary arteries, respectively.

It will be appreciated that the expandable support member 12 can be placed at other pulmonary arterial bifurcations 114, such as those described above. As shown in FIG. 21, for example, a first expandable support member 12 can be placed at a bifurcation 114 comprising the intersection of the right pulmonary artery 104, the upper branch 110 of the right pulmonary artery, and the lower branch 112 of the right pulmonary artery. Additionally, a second expandable support member 12 can be placed at a bifurcation 114 comprising the intersection of the left pulmonary artery 104, the upper branch 106 of the left pulmonary artery, and the lower branch 108 of the left pulmonary artery.

Figure 22:
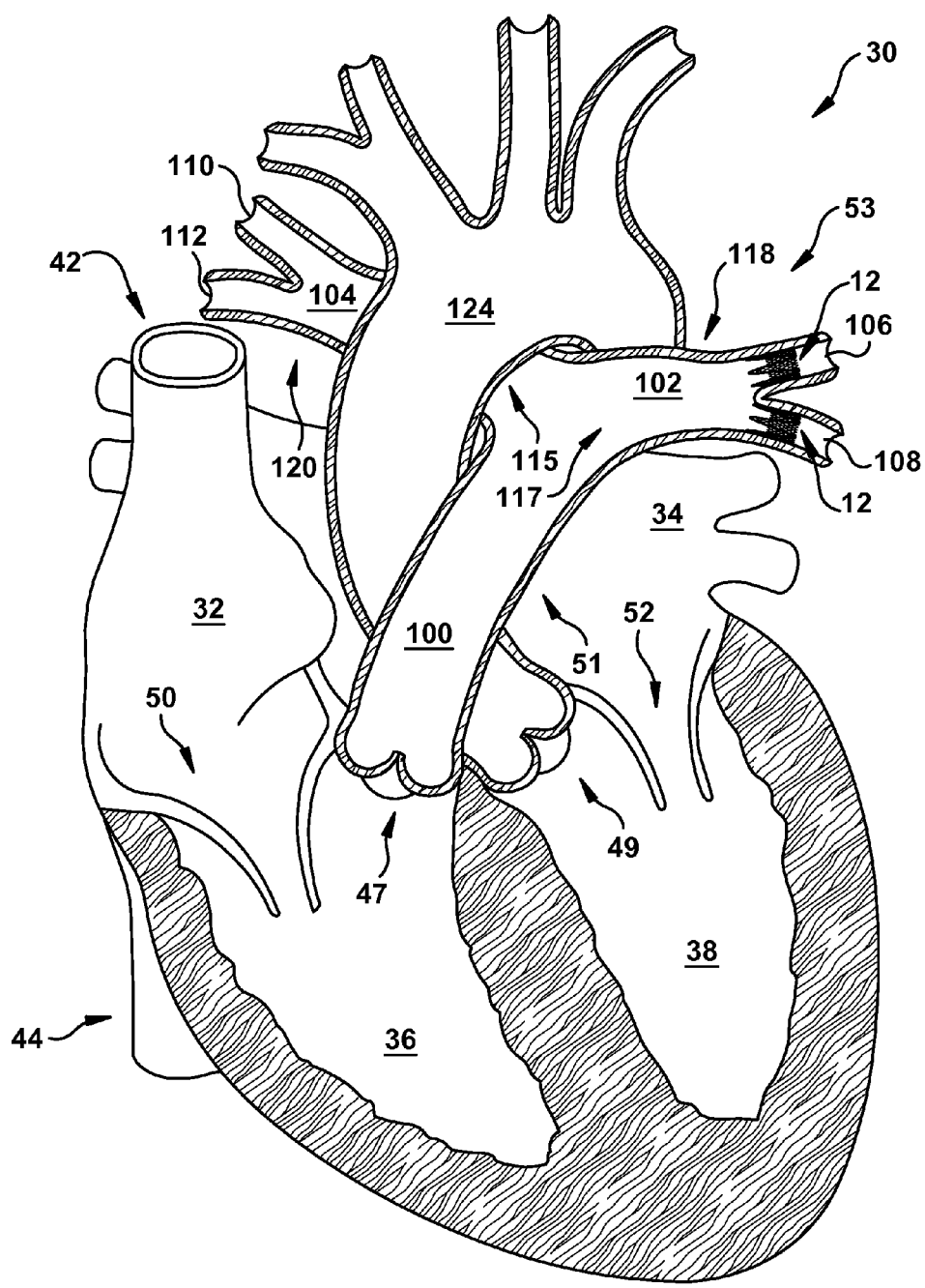
FIG. 22 is a schematic illustration of the human heart in FIG. 16 showing first and second apparatus deployed in the branches of the left pulmonary artery.

It will also be appreciated that an expandable support member 12, such as the one illustrated in FIG. 5 can be implanted at a pulmonary arterial bifurcation 114. As shown in FIG. 22, for example, a first expandable support member 12 can be implanted at a bifurcation 114 comprising the intersection of the left pulmonary artery 102, the upper branch 106 of the left pulmonary artery, and the lower branch 108 of the left pulmonary artery. The first expandable support member 12 can be implanted at the bifurcation 114 so that the main body portion 18 engages the vessel wall of the upper branch 106, and at least one wing member 26 engages the vessel wall of the left pulmonary artery 102. Additionally, a second expandable support member 12 can be implanted at a bifurcation 115 or 117 so that the main body portion 18 engages the vessel wall of the lower branch 108, and at least one wing member 26 engages the vessel wall of the left pulmonary artery 102.

Figure 23:
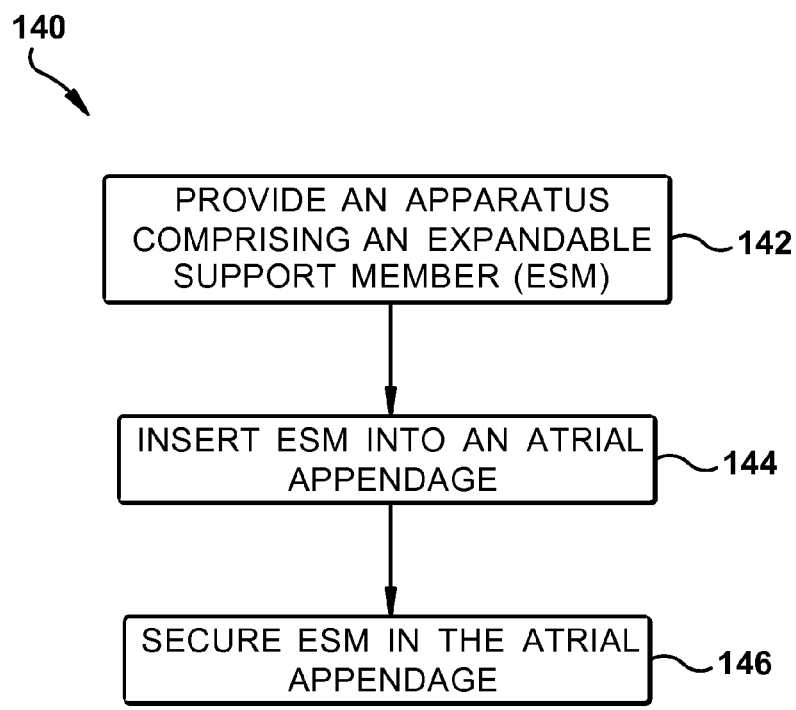
FIG. 23 is a process flow diagram illustrating a method for treating a cardiovascular disease according to another embodiment of the present invention.

FIG. 23 is a process flow diagram illustrating another embodiment of the present invention. In FIG. 23, a method 140 is provided for treating a cardiovascular disease, such as AF in a subject. One step of the method 140 can include providing an apparatus 10 at 142. The apparatus 10 can be identically or similarly constructed as the apparatus shown in FIGS. 1 and 3-7, as well as other configurations described herein. For example, the apparatus 10 can comprise an expandable support member 12 having oppositely disposed proximal and distal end portions 14 and 16 and a main body portion 18 extending between the end portions. The proximal end portion 14 can comprise a plurality of wing members 26 extending from the main body portion 18.

At least a portion of the expandable support member 12 can be treated with at least one therapeutic agent for eluting into an atrial chamber and/or cardiac tissue. For example, each of the wing members 26 can be treated with an anti-arrhythmic agent, such as a quinidine derivative while the main body portion 18 is treated with a different anti-arrhythmic agent, such as amioradone (or any of the other agents described above). Other examples of therapeutic agents that may be used to differentially treat separate portions of the apparatus 10 are described above.

Figure 24:
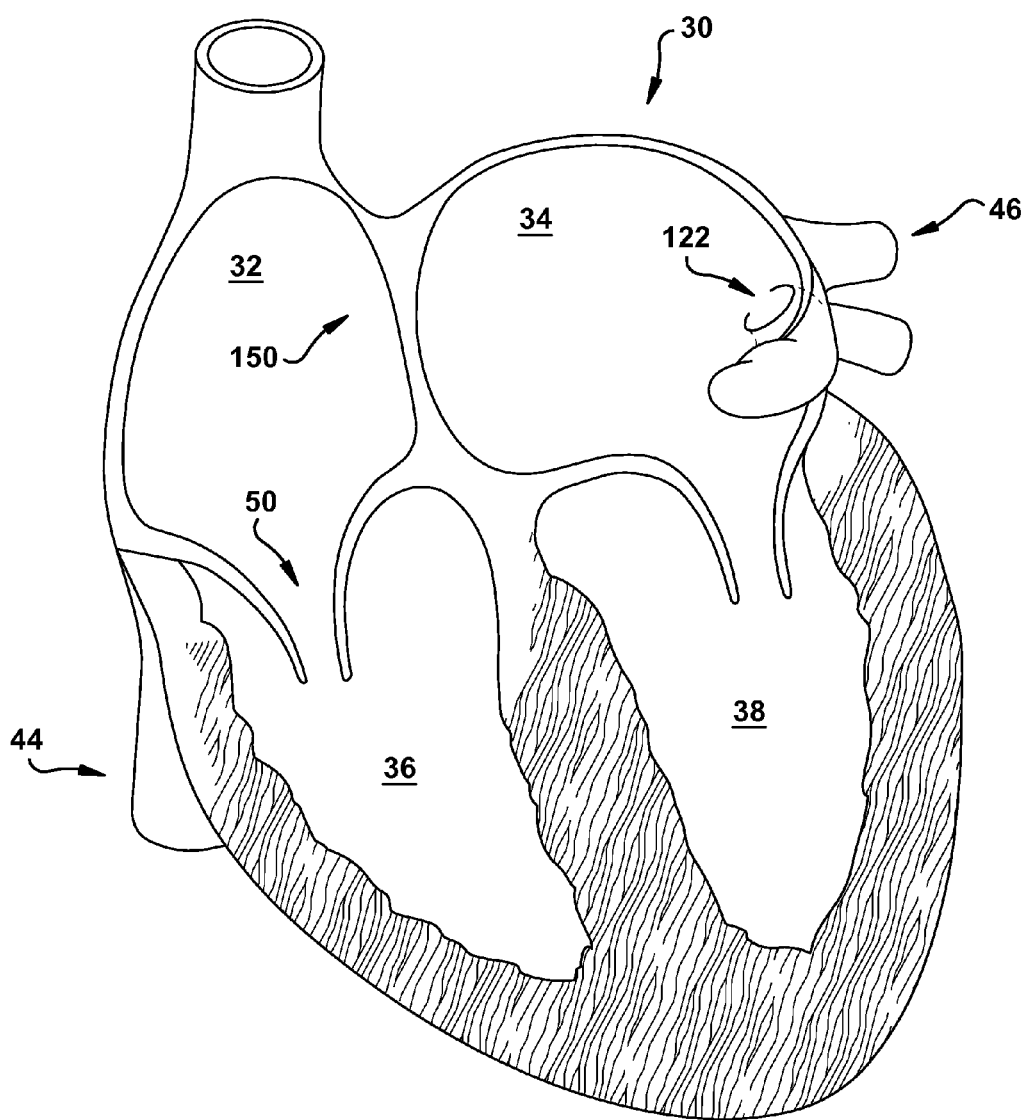
FIG. 24 is a schematic illustration of a human heart with emphasis on a left atrial appendage (LAA)

At 144, the expandable support member 12 can be inserted into an atrial appendage, such as a left atrial appendage 122 (LAA) (FIG. 24). The LAA 122 is derived from the left wall of the primary atrium, which forms during the fourth week of embryonic development. It has developmental, ultrastructural, and physiological characteristics distinct from the left atrium 34 proper. The LAA 122 lies within the confines of the pericardium in close relation to the free wall of the left ventricle 38, and thus its emptying and filling may be significantly affected by left ventricular function. Although the method 140 is described below with reference to implanting the expandable support member 12 in the LAA 122, it will be appreciated that the expandable support member may alternatively or additionally be placed in a right atrial appendage (not shown).

Prior to inserting the expandable support member 12 into the LAA 122, the dimensions of the LAA should be determined. Various devices and methods for determining the dimensions of cardiac vascular structures are known in the art. Once the dimensions of the LAA 122 have been determined, an appropriately-sized expandable support member 12 can be selected. More particularly, the selected expandable support member 12 will be appropriately-dimensioned to the size and shape of the LAA 122.

Figure 25:
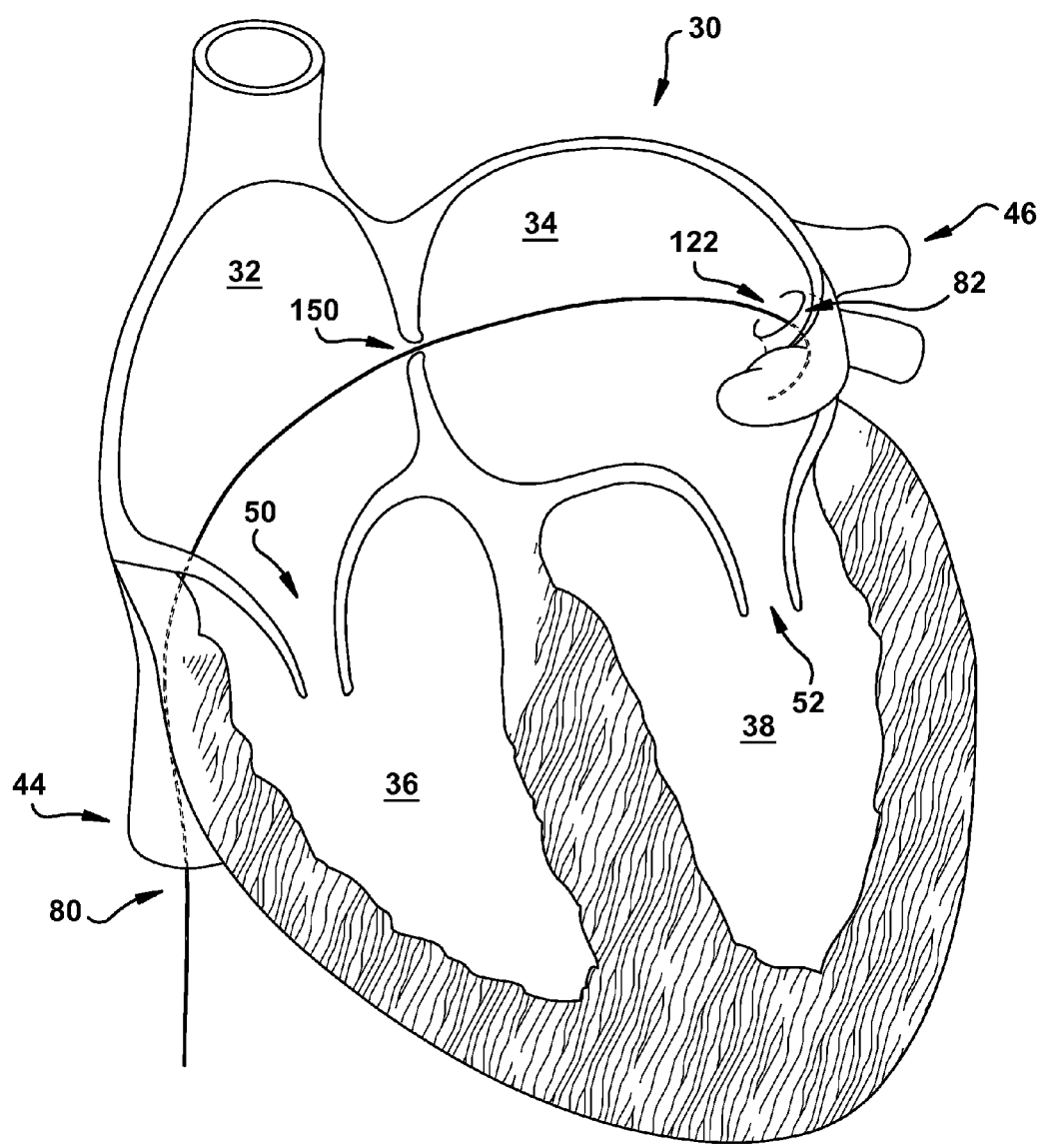
FIG. 25 is a schematic illustration of the human heart in FIG. 24 showing a guidewire being extended trans-septally into the LAA.

Next, a trans-septal approach can be used to place the expandable support member 12 in the LAA 122. For example, a guidewire 80 (FIG. 25) can be inserted into a femoral vein (not shown) or jugular vein (not shown) and, under image guidance (e.g., fluoroscopy, ultrasound, magnetic resonance, computed tomography, or a combination thereof), steered through the subject's vasculature into the inferior vena cava 44. As shown in FIG. 25, the guidewire 80 can then be passed into the right atrium 32, across the septum 150, into the left atrium 34, and into the LAA 122.

In an example of the trans-septal approach, a curved needle (not shown in detail), such as a 70 cm curved Brockenbrough needle (USCI, Billerica, Mass.) and a guidewire 80 (e.g., 0.014 inch PTCA guidewire) can be inserted into the stopcock lumen of the needle with an introducer (not shown) to determine the safety of the guidewire and the needle. For the Inoue technique, a dilator (e.g., a Mullins dilator) (not shown) alone can be advanced to the junction of superior vena cava 42 and right atrium 32 over a guidewire 80 (e.g., a 0.032 inch Terumo J guidewire) from the right femoral vein (not shown). After removing the 0.032 inch Terumo J guidewire, the Brockenbrough needle with a 0.014 inch guidewire can be advanced through the Mullins dilator. To avoid perforation of the dilator wall during needle advancement, the 0.014 inch guidewire can be protruded slightly beyond the tip of the needle and then moved in combination (i.e., the needle-wire combination) through the Mullins dilator. The septal puncture can be performed by pulling the 0.014 inch guidewire slightly below the tip of the needle. The angle of the needle for penetration of the septum 40 can be determined by using dimensions from a previous contrast-enhanced CT scan of the left atrium 34. For example, the CT slice showing the longest length of the atrial septum 40 can be used to determine the angle of the needle. The angle of the needle puncture can then be determined simply as the perpendicular angle of the atrial septum 40.

Figure 26:
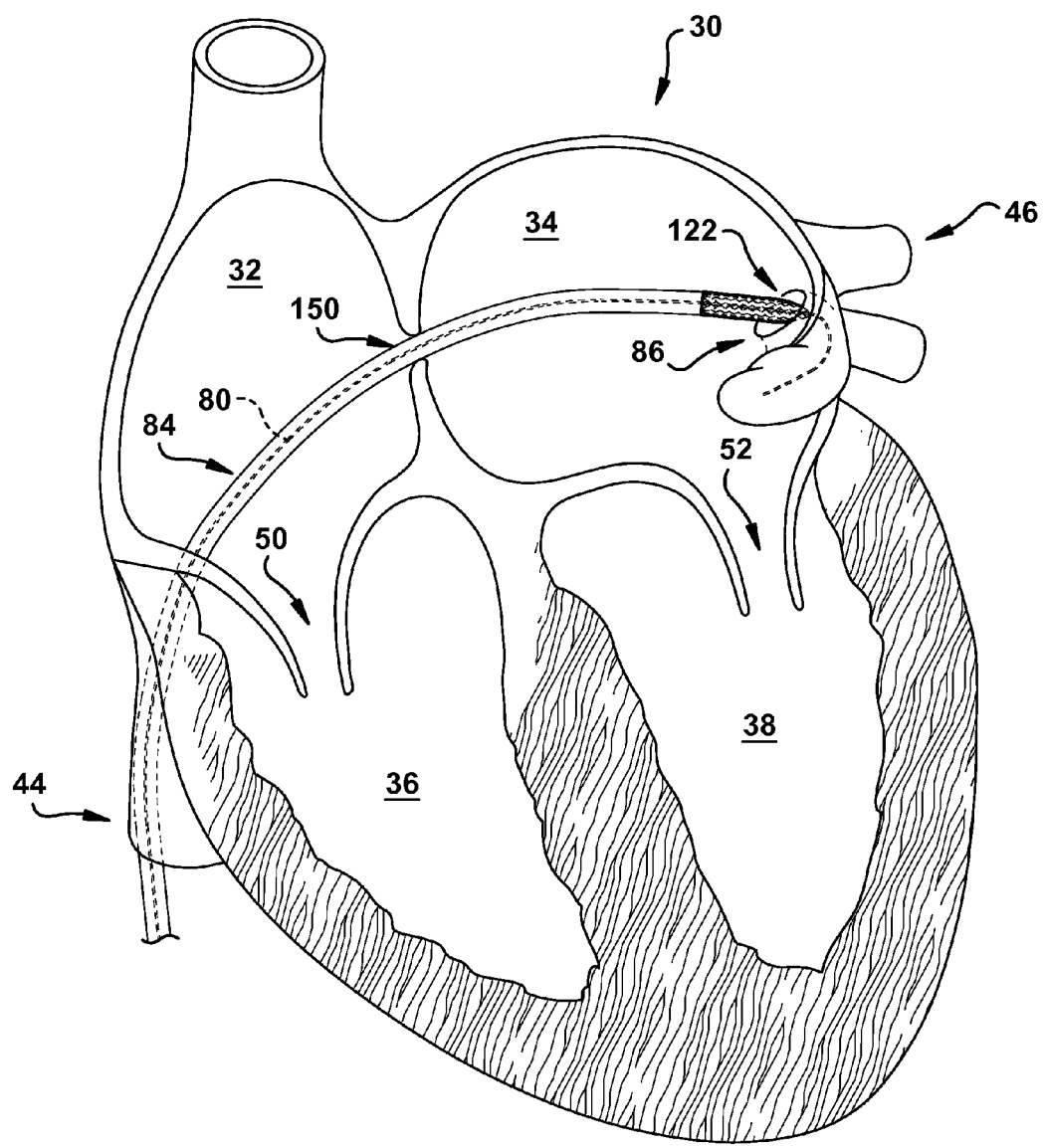
FIG. 26 is a schematic illustration of the human heart in FIG. 25 showing the apparatus in FIG. 1A being delivered to the LAA via a catheter.

After the guidewire 80 has been placed in the LAA 122, a catheter 84 or sheath can be passed over the guidewire as shown in FIG. 26. The catheter 84 may be comprised of a flexible, resiliently yieldable material such, as silicone, PTFE, ePTFE, plastic polymer, or the like. The catheter 84 can be urged along the guidewire 80 until the distal end 86 of the catheter is appropriately positioned at or in the LAA 122.

At 146, the expandable support member 12 can be placed into a collapsed configuration, attached to a proximal end (not shown) of the guidewire 80, and then advanced to the LAA 122 using a pushrod 92 (FIG. 27) or other similar device. Once the expandable support member 12 has been positioned near the distal end 86 of the catheter 84, the catheter can be slowly withdrawn to secure the expandable support member in the LAA 122. As the catheter 84 is withdrawn, the main body portion 18 can be progressively freed from the catheter and self-expand into contact with the ostium 126 of the LAA 122 (FIG. 27).

As the expandable support member 12 is further freed from the catheter 84, the wing members can 26 expand into their radially expanded configuration (FIG. 28) so that the wing members engage a portion of the antrum 72 surrounding the LAA 122. Once the expandable support member 12 has obtained its expanded configuration and is securely positioned in the LAA 122, the catheter 84 and guidewire 80 may be withdrawn from the subject. With the expandable support member 12 in place, the anti-arrhythmic agents can begin to elute into the left atrium 34 and/or surrounding vascular wall to normalize the heart rhythm of the subject.

It will be appreciated that the expandable support member 12 may be treated with an agent for treating an arrhythmia (e.g., atrial fibrillation) and then placed (as described above) into the LAA 122. With the expandable support member 12 securely positioned in the LAA 122, the agent can elute into the left atrium 34, through the mitral valve 52 into the left ventricle 38, and into the pulmonary vasculature 53.

Figure 27:
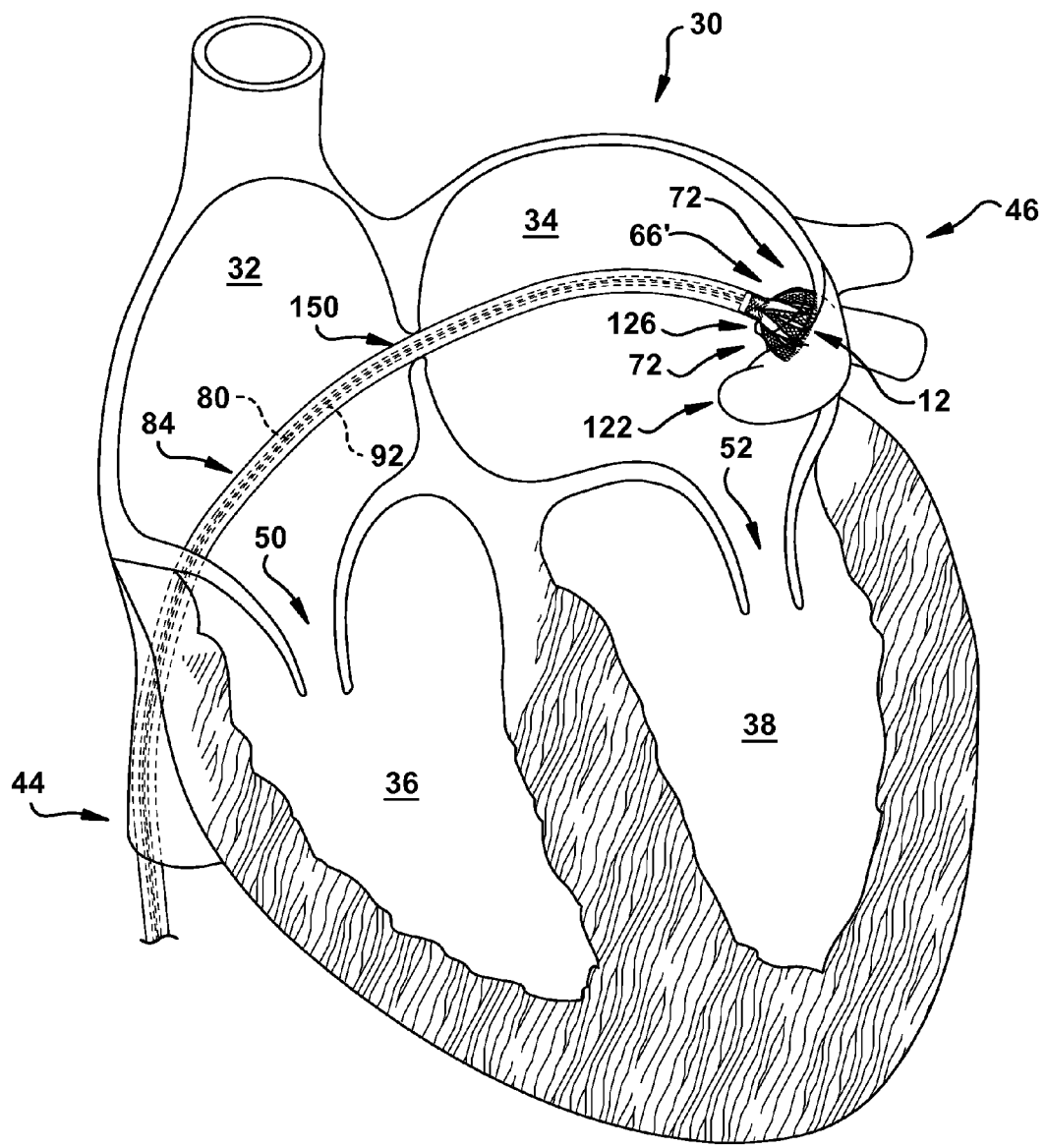
FIG. 27 is a magnified cross-sectional view of the left atrium showing the apparatus being deployed in the LAA.
Figure 28:
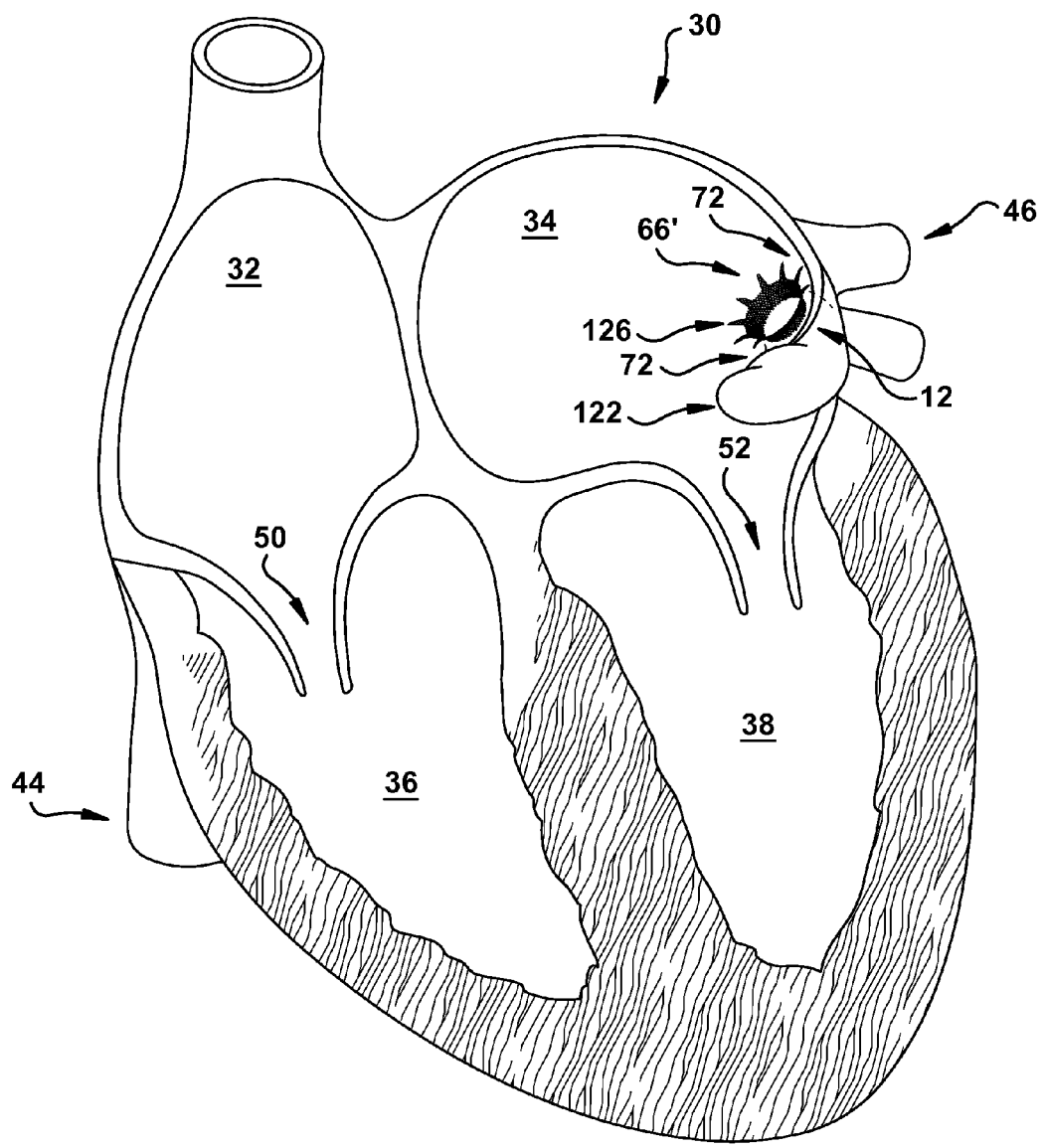
FIG. 28 is a magnified cross-sectional view of the left atrium showing the apparatus deployed in the LAA.

Although not illustrated in FIGS. 27 and 28, it should be understood that the expandable support member 12 can alternatively be placed in the LAA 122 such that the wing members 26 extend into and contact the cardiac walls comprising the LAA. In such a configuration, the main body portion 18 can be positioned so that the main body portion is also in contact with the cardiac walls comprising the LAA and/or the ostium 66' of the LAA 122.

It will also be appreciated that a percutaneous retrograde approach can be used to place the expandable support member 12 in the LAA 122. Briefly, for example, a guidewire 80 can be inserted into a femoral artery (not shown) or jugular artery (not shown), steered through the subject's vasculature into the aortic arch 124 into the left ventricle 38, across the mitral valve 52, into the left atrium 34, and into the LAA 122. A catheter 84 can then be passed over the guidewire 80 and urged along until the distal end 86 is positioned at or in the LAA 122. The expandable support member 12 can then be advanced to the LAA 122 and the catheter 84 slowly withdrawn to secure the expandable support member in the LAA.

Additionally, it should be appreciated that any of the apparatus 10 described herein can be removed from the subject once substantially all of the at least one therapeutic agent has eluted from the apparatus. After removing the apparatus 10 from the subject, another identical or similar apparatus that includes the same or similar therapeutic agent can again be implanted in the subject. This process ensures that the at least one therapeutic agent is continuously delivered to the subject as needed.

From the above description of the invention, those skilled in the art will perceive improvements, changes and modifications. For example, it is contemplated that in addition to the self-expanding apparatus 10 disclosed herein, a balloon (not shown) or mechanical-based apparatus (not shown) could be used to deliver and deploy the expandable support member 12. Additionally, it is contemplated that the apparatus 10 may be implanted in other cardiac structures, such as a coronary structure (not shown) or some other vascular bifurcation. Such improvements, changes, and modifications are within the skill of the art and are intended to be covered by the appended claims.

Having described the invention, we claim:

1. A method for treating a cardiovascular disease, said method comprising the steps of:

providing an apparatus comprising an expandable support member having oppositely disposed proximal and distal end portions and a main body portion extending between the end portions, the proximal end portion comprising a plurality of wing members extending from the main body portion, at least a portion of the expandable support member being treated with at least one therapeutic agent for eluting into a blood vessel;

inserting the expandable support member into the pulmonary vasculature;

advancing the expandable support member to a bifurcation in the pulmonary vasculature, the bifurcation comprising the intersection of a first pulmonary blood vessel, a second pulmonary blood vessel, and third pulmonary blood vessel; and securing the expandable support member within the bifurcation so that the wing members engage a portion of the vessel wall in both the second and third pulmonary blood vessels;

wherein the at least one therapeutic agent elutes into the pulmonary vasculature to treat the cardiovascular disease;

wherein the cardiovascular disease is selected from the group consisting of arrhythmias, heart failure, acute and chronic heart transplant rejection, and pulmonary arterial hypertension.

2. The method of claim 1, where said step of securing the expandable support member at the bifurcation further includes expanding the expandable support member so that the at least one wing member and the main body portion engage a portion of the arterial wall at the bifurcation.

3. The method of claim 2 wherein said step of expanding the expandable support member further includes the steps of:
positioning the at least one wing member at the bifurcation so that the at least one wing member engages a portion of the left pulmonary artery;
positioning a second wing member at the bifurcation so that the second wing member engages a portion of the right pulmonary artery; and
positioning the main body portion at the bifurcation so that the main body portion engages a portion of the pulmonary artery.

4. The method of claim 2, wherein said step of expanding the expandable support member further includes the steps of:
positioning the main body portion at the bifurcation so that the main body portion engages a portion of the left pulmonary artery; and
positioning the at least one wing member at the bifurcation so that the at least one wing member engages a portion of the pulmonary artery.

5. The method of claim 3 further including the steps of:
providing a second apparatus comprising a second expandable support member having oppositely disposed proximal and distal end portions and a second main body portion extending between the end portions, the proximal end portion comprising a plurality of wing members extending from the second main body portion, at least a portion of the second expandable support member being treated with at least one therapeutic agent for eluting into a blood vessel;
inserting the second expandable support member into the pulmonary vasculature;
advancing the second expandable support member to a second bifurcation in the pulmonary vasculature; and
securing the second expandable support member at the second bifurcation;
wherein the at least one therapeutic agent elutes into the pulmonary vasculature to treat the cardiovascular disease.

6. The method of claim 5, wherein said step of securing the second expandable support member at the second bifurcation further includes the steps of:
positioning the second main body portion so that the second main body portion engages a portion of an upper branch of the left pulmonary artery; and
positioning at least one wing member of the second expandable support member so that the at least one wing member engages a portion of the left pulmonary artery.

7. The method of claim 5, wherein said step of securing the second expandable support member at the second bifurcation further includes the steps of:
positioning the second main body portion so that the second main body portion engages a portion of an upper branch of the right pulmonary artery; and
positioning at least one wing member of the second expandable support member so that the at least one wing member engages a portion of the right pulmonary artery.

8. The method of claim 1, wherein said step of inserting the expandable support member into the pulmonary vasculature is done percutaneously via an intravascular catheter.

9. The method of claim 8 further comprising expanding the expandable support member with an expandable balloon.

10. The method of claim 8 further comprising the steps of:
delivering the expandable support member to the bifurcation via the catheter in a collapsed configuration; and
removing the catheter so that the expandable support member self-expands into the bifurcation.

11. The method of claim 1, wherein the cardiovascular disease is pulmonary arterial hypertension.

12. The method of claim 1, wherein at least a portion of the expandable support member is made from a bioabsorbable material.

13. A method for treating a cardiovascular disease, said method comprising the steps of:
providing an apparatus comprising an expandable support member having oppositely disposed proximal and distal end portions and a main body portion extending between the end portions, the proximal end portion comprising a plurality of wing members extending from the main body portion, at least a portion of the expandable support member being treated with at least one therapeutic agent for eluting into an atrial chamber and/or cardiac tissue;
inserting the expandable support member into an atrial appendage, the atrial appendage having an ostium surrounded by an antrum of the atrial chamber, the atrial appendage being structurally and physiologically distinct from the atrial chamber; and
securing the expandable support member in the atrial appendage.

14. The method of claim 13, wherein said step of securing the expandable support member in the atrial appendage further comprises expanding the expandable support member so that a portion of the main body portion engages the ostium and at least one wing member engages a portion of the antrum surrounding the ostium.

15. The method of claim 14, wherein said step of inserting the expandable support member into the atrial appendage is done percutaneously via an intravascular catheter.

16. The method of claim 15 further comprising expanding the expandable support member with an expandable balloon.

17. The method of claim 15 further comprising the steps of:
delivering the expandable support member to the atrial appendage via the catheter in a collapsed configuration; and
removing the catheter so that the expandable support member self-expands into the atrial appendage.

18. The method of claim 13, wherein the atrial appendage is a left atrial appendage.

19. The method of claim 13, wherein the cardiovascular disease is an arrhythmia.

20. The method of claim 13, wherein at least a portion of the expandable support member is made from a bioabsorbable material.

21. A method for treating a cardiovascular disease, said method comprising the steps of:
  providing an apparatus comprising an expandable support member and an electrical mechanism coupled to the expandable support member, the expandable support member having oppositely disposed proximal and distal end portions and a main body portion extending between the end portions, the proximal end portion comprising a plurality of wing members extending from the main body portion, at least a portion of the expandable support member being treated with at least one therapeutic agent for eluting into a blood vessel, the electrical mechanism for delivering electrical energy to at least a portion of the ostium of a pulmonary blood vessel to ablate tissue;
  inserting the expandable support member into the pulmonary vasculature;
  advancing the expandable support member to a bifurcation in the pulmonary vasculature, the bifurcation comprising the intersection of a first pulmonary blood vessel, a second pulmonary blood vessel, and third pulmonary blood vessel; and
  securing the expandable support member within the bifurcation so that the wing members engage a portion of the vessel wall in both the second and third pulmonary blood vessels;
  wherein the at least one therapeutic agent elutes into the pulmonary vasculature to treat the cardiovascular disease;
  wherein the cardiovascular disease is selected from the group consisting of arrhythmias, heart failure, acute and chronic heart transplant rejection, and pulmonary arterial hypertension.

22. The method of claim 21, further comprising activating the electrical mechanism to deliver electrical energy to the at least a portion of the ostium of the pulmonary blood vessel to ablate tissue.

23. The method of claim 1, wherein said step of providing an apparatus further includes providing an expandable support member having each of the wing members separately spaced apart from one another.

24. The method of claim 1, wherein said step of providing an apparatus further includes providing an expandable support member having each of the wing members radially spaced apart from one another.

25. The method of claim 23, wherein each of the wing members resembles an arch.

* * * * *